United States Patent
Burbank et al.

(10) Patent No.: US 7,172,603 B2
(45) Date of Patent: Feb. 6, 2007

(54) DEPLOYABLE CONSTRICTOR FOR UTERINE ARTERY OCCLUSION

(75) Inventors: Fred H. Burbank, Laguna Niguel, CA (US); Michael L. Jones, San Clemente, CA (US); Greig E. Altieri, Laguna Beach, CA (US); Ed Olson, Lake Forest, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 748 days.

(21) Appl. No.: 10/300,495

(22) Filed: Nov. 19, 2002

(65) Prior Publication Data

US 2004/0097962 A1 May 20, 2004

(51) Int. Cl.
*A61B 17/42* (2006.01)
(52) U.S. Cl. ..................................... 606/119
(58) Field of Classification Search ............... 606/158, 606/142, 151, 119
See application file for complete search history.

(56) References Cited

U.S. PATENT DOCUMENTS

| | | | |
|---|---|---|---|
| 2,400,251 | A | 5/1946 | Nagel |
| 3,209,753 | A | 10/1965 | Hawkins et al. |
| 3,411,505 | A | 11/1968 | Nobis |
| 3,777,740 | A | 12/1973 | Hokanson |
| 4,292,960 | A | 10/1981 | Paglione |
| 4,428,374 | A | 1/1984 | Auburn |
| 4,428,379 | A | 1/1984 | Robbins et al. |
| 4,509,528 | A | 4/1985 | Sahota |
| 4,650,466 | A | 3/1987 | Luther |
| 4,757,823 | A | 7/1988 | Hofmeister et al. |
| 4,945,896 | A | 8/1990 | Gade |
| 4,991,588 | A | 2/1991 | Pflueger et al. |
| 4,994,069 | A | 2/1991 | Ritchart et al. |
| 5,037,430 | A | 8/1991 | Hasson |
| 5,037,433 | A | 8/1991 | Wilk et al. |
| 5,081,997 | A | 1/1992 | Bosley, Jr. et al. |
| 5,108,408 | A | 4/1992 | Lally |

(Continued)

FOREIGN PATENT DOCUMENTS

DE 195 28 440 A 2/1997

(Continued)

OTHER PUBLICATIONS

International Search Report for PCT/US2004/038111, mailed May 3, 2005.

(Continued)

*Primary Examiner*—(Jackie) Tan-Uyen T. Ho

(57) ABSTRACT

Devices, systems and methods for occluding blood vessels include a deployable constrictor having opposed pressure-applying portions, a delivery shaft configured to intravaginally advance the constrictor to the patient's cervix, a location sensor configured to detect a blood vessel, a deployment member for deploying the constrictor about the patient's cervix, and optionally a guide. The constrictor has a first configuration to receive a cervix and a second configuration to apply pressure to the cervical area to occlude a uterine artery by compression from the pressure-applying members. The pressure-applying members may be released from the cervix after a limited therapeutically effective time. The constrictor is for treating uterine disorders and conditions which may be treated by occlusion of the uterine arteries, such as uterine fibroids, dysfunctional uterine bleeding, post-partum hemorrhage, and bleeding associated with caesarian sections.

43 Claims, 12 Drawing Sheets

U.S. PATENT DOCUMENTS

| | | | |
|---|---|---|---|
| 5,201,314 A | 4/1993 | Bosley et al. |
| 5,226,911 A | 7/1993 | Chee et al. |
| 5,275,166 A | 1/1994 | Vaitekunas et al. |
| 5,289,831 A | 3/1994 | Bosley |
| 5,336,229 A | 8/1994 | Noda |
| 5,336,231 A | 8/1994 | Adair |
| 5,383,922 A | 1/1995 | Zipes et al. |
| 5,456,693 A | 10/1995 | Conston et al. |
| 5,458,596 A | 10/1995 | Lax et al. |
| 5,488,958 A | 2/1996 | Topel et al. |
| 5,496,331 A | 3/1996 | Xu et al. |
| 5,507,744 A | 4/1996 | Tay et al. |
| 5,542,944 A | 8/1996 | Bhatta |
| 5,549,624 A | 8/1996 | Mirigian et al. |
| 5,549,824 A | 8/1996 | Trumpf et al. |
| 5,556,396 A | 9/1996 | Cohen et al. |
| 5,570,692 A | 11/1996 | Morinaga |
| 5,588,960 A | 12/1996 | Edwards et al. |
| 5,598,841 A | 2/1997 | Taniji et al. |
| 5,614,204 A | 3/1997 | Cochrum |
| 5,658,299 A | 8/1997 | Hart |
| 5,662,680 A | 9/1997 | Desai |
| 5,665,096 A | 9/1997 | Yoon |
| 5,672,153 A | 9/1997 | Lax et al. |
| 5,672,172 A | 9/1997 | Zupkas |
| 5,691,314 A | 11/1997 | Hodgen |
| 5,697,942 A | 12/1997 | Palti |
| 5,702,407 A | 12/1997 | Kaji |
| 5,713,371 A | 2/1998 | Sherman et al. |
| 5,713,896 A | 2/1998 | Nardella |
| 5,713,942 A | 2/1998 | Stern et al. |
| 5,715,832 A | 2/1998 | Koblish et al. |
| 5,716,389 A | 2/1998 | Walinsky et al. |
| 5,720,743 A | 2/1998 | Bischof et al. |
| 5,749,879 A | 5/1998 | Middleman et al. |
| 5,759,154 A | 6/1998 | Hoyns |
| 5,766,135 A | 6/1998 | Terwilliger |
| 5,776,129 A | 7/1998 | Mersch |
| 5,792,059 A | 8/1998 | Furia et al. |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,895,395 A | 4/1999 | Yeung |
| 5,899,861 A | 5/1999 | Friemel et al. |
| 5,904,651 A | 5/1999 | Swanson et al. |
| 5,910,484 A | 6/1999 | Haupert, Jr. |
| 5,911,691 A | 6/1999 | Mochizuki et al. |
| 5,916,173 A | 6/1999 | Kirsner |
| 5,921,933 A | 7/1999 | Sarkis et al. |
| 5,941,889 A | 8/1999 | Cermak |
| 5,979,453 A | 11/1999 | Savage et al. |
| 6,013,088 A | 1/2000 | Karavidas |
| 6,015,541 A | 1/2000 | Greff et al. |
| 6,019,724 A | 2/2000 | Gronningsaeter et al. |
| 6,032,673 A | 3/2000 | Savage et al. |
| 6,033,398 A | 3/2000 | Farley et al. |
| 6,034,477 A | 3/2000 | Peeters et al. |
| 6,035,238 A | 3/2000 | Ingle et al. |
| 6,045,508 A | 4/2000 | Hossack et al. |
| 6,066,139 A | 5/2000 | Ryan et al. |
| 6,077,257 A | 6/2000 | Edwards et al. |
| 6,080,118 A | 6/2000 | Blythe |
| 6,096,051 A | 8/2000 | Kortenbach et al. |
| 6,106,473 A | 8/2000 | Violante et al. |
| 6,169,914 B1 | 1/2001 | Hovland et al. |
| 6,175,751 B1 | 1/2001 | Maizes |
| 6,210,330 B1 | 4/2001 | Tepper |
| 6,231,515 B1 | 5/2001 | Moore et al. |
| 6,254,601 B1 | 7/2001 | Burbank et al. |
| 6,261,234 B1 | 7/2001 | Lin |
| 6,280,441 B1 | 8/2001 | Ryan |
| 6,368,340 B2 | 4/2002 | Malecki et al. |
| 6,425,867 B1 | 7/2002 | Vaezy et al. |
| 6,905,506 B2 | 6/2005 | Burbank et al. |
| 2002/0165579 A1 | 11/2002 | Burbank et al. |
| 2002/0183771 A1 | 12/2002 | Altieri et al. |
| 2003/0120306 A1 | 6/2003 | Burbank et al. |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 A | 1/1997 |
| GB | 2 311 468 A | 1/1997 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 02/39904 A1 | 5/2002 |
| WO | WO 02/078521 | 10/2002 |

OTHER PUBLICATIONS

Written Opinion for PCT/US2004/038111, mailed May 3, 2005.

Translation of FR 1 220 773.

International Search Report for PCT/US03/35815 mailed Jun. 30, 2004.

Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

Bateman, William M.D., "Treatment of intractable menorrhagia by bilateral uterine vessel, Interruption", *Am. J. Obst. & Gynec.* 89(6):825-827 (Jul. 15, 1964).

Brigato, G. et al., "A Nonivasive Instrument Method in Severe Postpartum Hemorrhages", *Minerva Ginecologica* 50(7-8):337-339 (1998).

Brohim, Robert M. et al., "Development of Independent Vessel Security After Ligation With Absorbable Sutures or Clips", *The American Journal of Surgery*, Mar. 1993, vol. 165, pp. 345-348.

Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737-739.

Hunerbien, M. et al., "Endoscopic Ultrasound-Guided Real Time Biopsy of Peri-Intestinal Tumors", *Surgical Technology International VII*, 1998, pp. 91-95.

O'Leary, James A., M.D. et al., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

International Search Report for PCT/US02/09745 mailed Sep. 12, 2002.

International Search Report for PCT/US02/23347 mailed Nov. 20, 2002.

International Search Report for EP 99 96 7154 (PCT/US99/28101) mailed Dec. 3, 2002.

International Search Report for PCT/US02/22015 mailed Dec. 3, 2002.

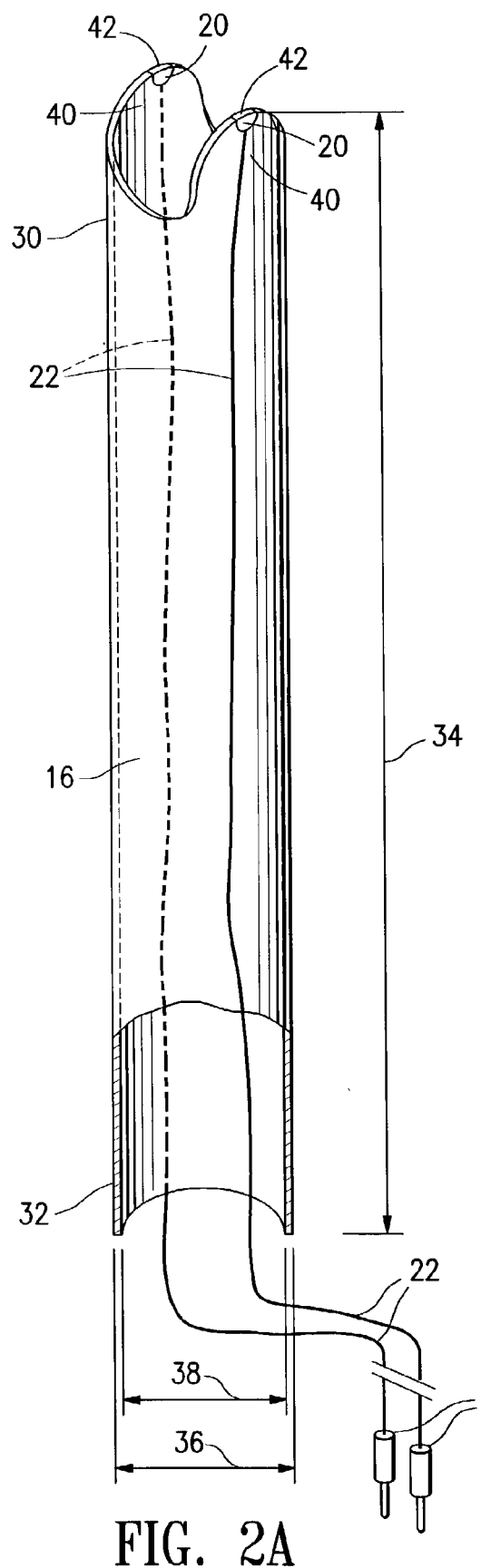
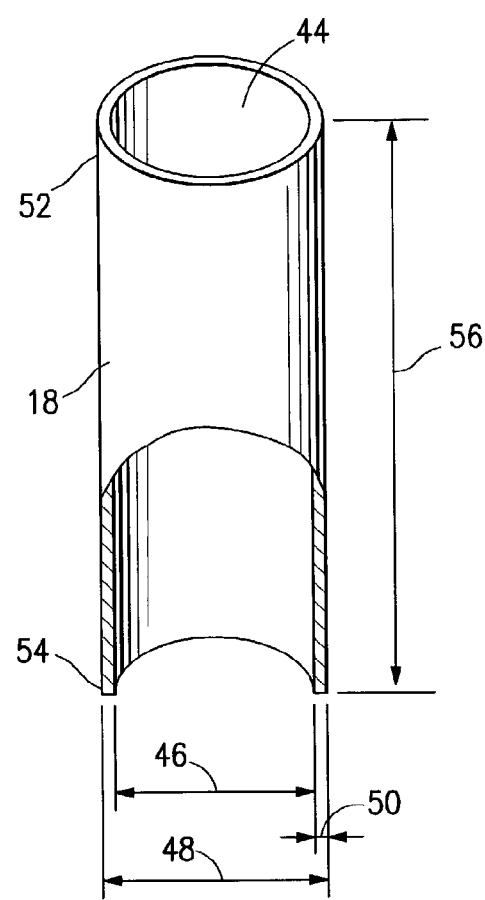
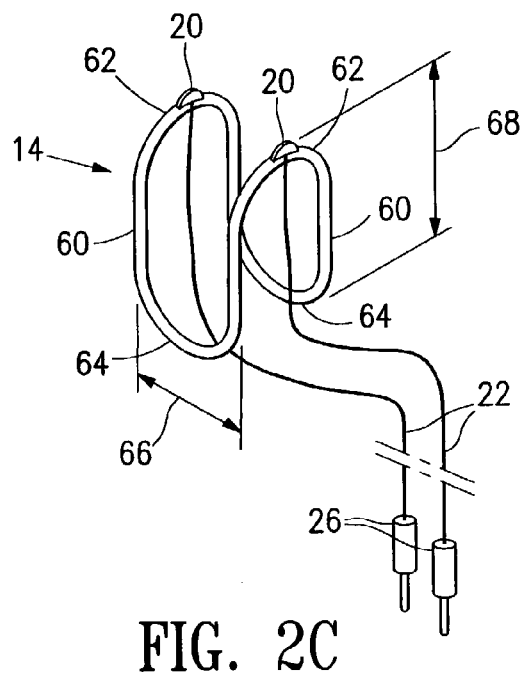
FIG. 2A
FIG. 2B
FIG. 2C

DEPLOYABLE CONSTRICTOR FOR UTERINE ARTERY OCCLUSION

FIELD OF THE INVENTION

The invention relates generally to the field of devices and methods for treating diseases and conditions by regulating blood flow in blood vessels. In particular, the invention is directed to the treatment of uterine conditions by detecting and reducing or abolishing blood flow to the uterus.

BACKGROUND OF THE INVENTION

Hysterectomy (surgical removal of the uterus) is performed on approximately 600,000 women annually in the United States. Hysterectomy is often the therapeutic choice for the treatment of uterine cancer, adenomyosis, menorrhagia, uterine prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, having many undesirable characteristics. Thus, any method which can approximate the therapeutic result of a hysterectomy without removing the uterus would be a significant improvement in this field. Newer treatment methods have been developed for some diseases which may spare these women a hysterectomy.

In 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sept. 9, 1995; Vol. 346; pp. 671–672, incorporated in its entirety herein). This technique is known as "uterine artery embolization". In this technique, uterine arteries are accessed via a transvascular route from a common femoral artery into the left and right uterine arteries.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms. See also Burbank, et al., "Uterine Artery Occlusion by Embolization or Surgery for the Treatment of Fibroids: A Unifying Hypothesis—Transient Uterine Ischemia," The Journal of the American Association of Gynecologic Laparoscopists, November 2000, Vol. 7, No.4 Supplement, pp. S3–S49. U.S. Pat. No. 6,254,601, to Burbank et al., entitled "Methods for Occlusion of the Uterine Arteries," describes numerous devices and methods useful for occluding a uterine artery by penetrating the tissue of the patient to access the uterine artery.

However, catheter-based uterine artery embolization under radiologic direction is a complicated procedure requiring highly sophisticated equipment. Accordingly, far fewer uterine artery embolizations than hysterectomies are performed for uterine fibroids which are symptomatic.

What is needed, therefore, are devices and methods to detect blood vessels and blood flow in blood vessels, and devices and methods to occlude blood flow in blood vessels such as the uterine arteries that can be easily used by physicians of ordinary skill in a simple medical setting or environment to aid in the therapeutic occlusion of arteries.

SUMMARY OF THE INVENTION

The invention is directed to detecting and occluding blood flow in a blood vessel effective to reduce or abolish blood flow in the blood vessel for therapeutic or diagnostic reasons, such as to treat uterine disorders such as uterine fibroids, dysfunctional uterine bleeding, and other uterine disorders.

An embodiment of a uterine artery occlusion device having features of the invention includes a deployable constrictor having at least one pressure-applying portion. The deployable constrictor has a first configuration for receiving a patient's cervix, and a second configuration for applying pressure to the patient's cervix or uterus upon its deployment. An elongate delivery shaft is provided to intravaginally advance the deployable constrictor to the patient's cervix in the first configuration. A deployment member such as a tube configured to deploy the constrictor from the delivery shaft onto or about the patient's cervix to at least partially occlude one or more uterine arteries. At least one lumen locating sensor is provided on a distal portion of the device to properly position the constrictor onto or about the cervix so that when it is deployed the pressure-applying portions of the constrictor occlude one or more uterine arteries. At least one lumen locating sensor may be disposed on a deployable constrictor, or on an elongate delivery shaft, or both. A constrictor having features of the invention may be, for example, a resilient member and configured with at least one loop, and preferably at least two loops, to engage and compress a portion of the patient's cervix and the constrictor may be a continuous wireform such as a coil, spring, or wire loop. In preferred embodiments, a constrictor may have at least two pressure-applying members.

The lumen locating sensor may be a blood flow sensor, a sound sensor, an ultrasound sensor, a pressure sensor, a pulsation sensor, a stress sensor, a strain sensor, a chemical sensor, an electromagnetic radiation sensor, or any combination of such sensors. A sensor is preferably a Doppler ultrasound sensor configured to emit and receive ultrasound energy. The sensor or sensors may be disposed on one or more pressure-applying portions of the constrictor, a distal portion of the delivery shaft, or both.

The elongate delivery shaft is configured to intravaginally advance a constrictor in the first expanded configuration to the patient's cervix and to position the constrictor about tissue near to the uterine arteries with the aid of the locating sensors. Preferably, the delivery shaft is configured to slidably fit within a lumen of the deployment member. The deployment member lumen is oriented generally in a longitudinal direction, and is configured to receive at least part of the delivery shaft as the deployment member moves longitudinally along and around the shaft. Such longitudinal motion of the deployment member over the delivery shaft forward is effective to deploy the constrictor from the delivery shaft and onto or about the cervix. The delivery shaft may be configured to engage a suitable guide, such as a tenaculum, guidewire, or the like.

A system having features of the invention may further include a guide member configured to engage a cervix, such as a tenaculum or guidewire to guide the delivery shaft to the patient's cervix and also to support the cervix in the desired position. A system having features of the invention may include a sensor controller to provide a signal related to the output of the locating sensor that may be readily interpreted or used by an operator. A sensor controller may regulate the operation of the locating sensor, and may include an energy source configured to provide energy for operating the locating sensor. A sensor controller may also include other elements or features configured to aid in generating, receiving, analyzing, or outputting sensor information.

The constrictor may be mounted on the distal end of the delivery shaft with at least the distal end of the constrictor in an opened condition to facilitate positioning about the cervix and optionally also the uterine body. The delivery shaft and mounted constrictor may be advanced through the patient's vaginal canal until adjacent to the patient's cervix. The output from the sensor on the distal portion of the device, i.e. the distal portion of the constrictor and/or the distal portion of the delivery shaft, may be used to guide the delivery shaft to a proper position about the cervix and optionally the uterine body. The distal ends of the constrictor may be pressed against the patient's vaginal fornix adjacent the cervix and uterus so that when the deployment member pushes the constrictor off the delivery shaft to deploy the constrictor, the pressure applying portions of the constrictor assume a pressure-applying configuration and press against the tissue about or adjacent the uterine arteries, thereby occluding them. For treating fibroids the constrictor should be in place or about 0.5 to about 24 hours, usually about 1 to about 9 hours.

The deployed constrictor may be removed by replacing the delivery shaft or similar device so as to expand the pressure-applying portion(s) and remount the constrictor onto the delivery shaft for removal. Such removal may be aided by a lanyard or similar device for applying tension during remounting on a delivery shaft; a lanyard may alternatively be used to remove a constrictor without the use of a delivery shaft. A deployed constrictor may also be removed by cutting a pressure-applying portion, or allowing a pressure-applying portion to expand or separate. A constrictor may also have a release mechanism which releases pressure on tissue after a suitable time, in response to a signal, under the influence of a lanyard, or otherwise as desired.

Methods embodying features of the invention include methods of occluding a uterine artery of a female human patient, the patient having a uterus, a cervix with a cervical os and a vaginal wall with a vaginal fornix, comprising pushing a pressure-applying member so as to distend the vaginal wall near the vaginal fornix near to a uterine artery, compressing the uterine artery with a pressure-applying member effective to reduce or abolish blood flow in the uterine artery. Compression may also be effective to retain in place a constrictor having a pressure-applying member. In embodiments of the devices, pressure-applying members comprise tissue-retaining features such as spikes, serration, rough surfaces, ridges, or scallops. Such tissue-retaining features are configured to prevent undesired movement of the pressure-applying members over the surface of the tissue to which they are attached.

The methods may further comprise detecting a reduction in blood flow through a uterine artery. A suitable guide, such as a tenaculum or guidewire, may be used to engage a cervix, preferably to manipulate the cervix so as to aid in placing the constrictor and in occluding the uterine arteries. The methods may further comprise releasing pressure applied to the cervix or uterus, so the pressure is applied for only a limited time and the uterine arteries are occluded for only a limited time. In preferred methods, the limited time is sufficient to reduce blood flow through a uterine artery to treat a condition of the uterus without causing undue damage or stress to the uterus.

The invention thus provides instruments and methods of utilizing such instruments for effective treatment of diseases and conditions that might otherwise require invasive and irreversible treatments such as removal of a patient's uterus. The devices and methods are simple and easy to use, simple to remove, and thus provide many advantages over other methods and devices. The invention provides improved treatments for serious conditions and diseases, including uterine fibroids, adenomyosis, dysfunctional uterine bleeding (DUB), postpartum hemorrhage, and other uterine disorders.

BRIEF DESCRIPTION OF THE DRAWINGS

FIG. 2A is a perspective view of a delivery shaft shown in FIG. 1.

FIG. 2B is a perspective view of a deployment member shown in FIG. 2.

FIG. 2C is a perspective view of a constrictor having features of the invention.

DETAILED DESCRIPTION OF THE PREFERRED EMBODIMENTS

Figure 1:
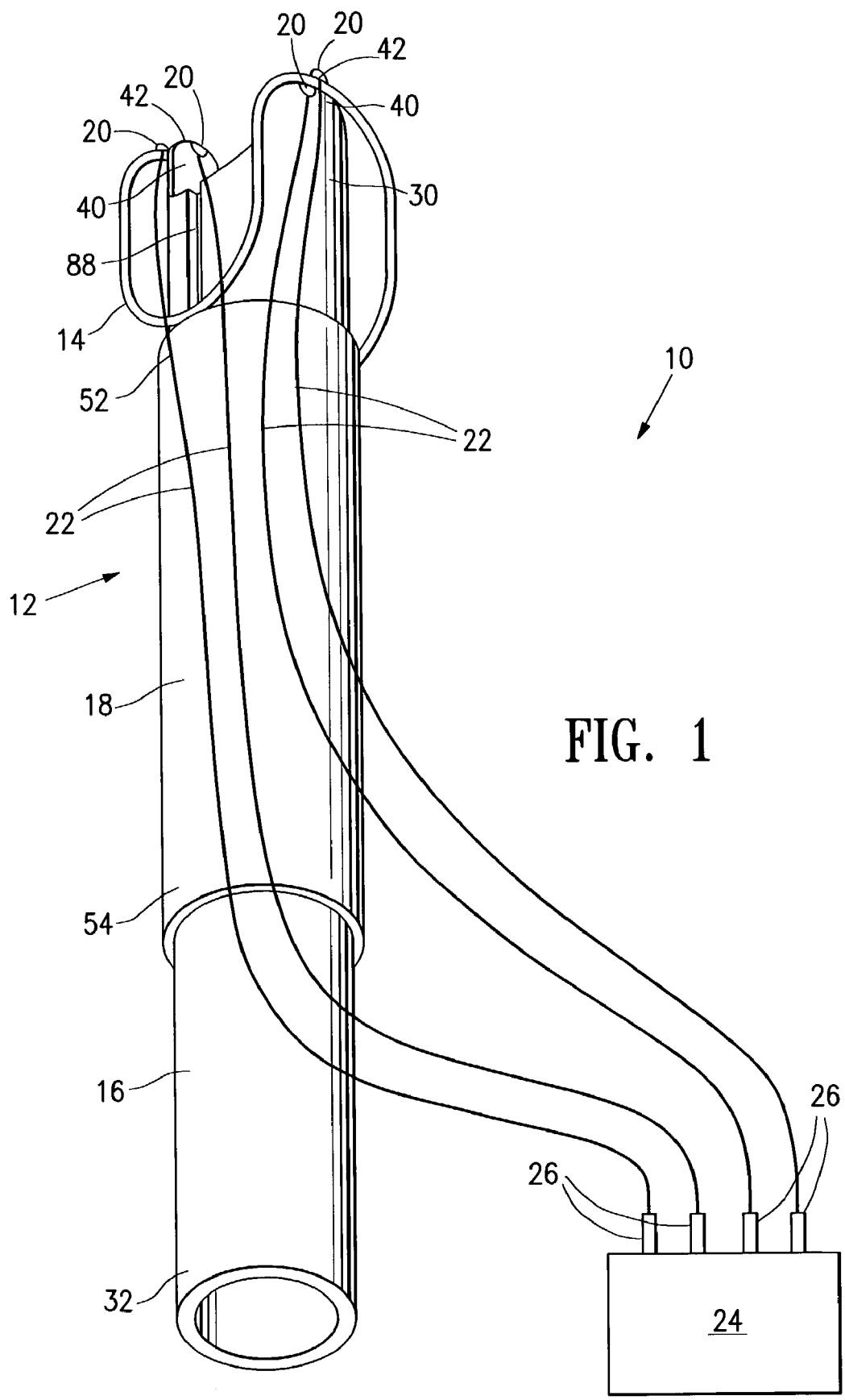
FIG. 1 is a perspective view of a system embodying features of the invention.

A system 10 embodying features of the invention is shown in FIG. 1. The system 10 includes an artery occlusion device 12 that has a tissue constrictor 14 mounted on the distal end of a delivery shaft 16, a deployment member 18, and a pair of location sensors 20 operatively connected to sensor cables 22. In the embodiment shown in FIG. 1, sensor cables 22 may be operatively connected to a sensor controller 24 with cable connectors 26 that are configured to allow ready connection and disconnection of the sensor cables 22 with the sensor controller 24. Where both a constrictor 14 and a delivery shaft 16 have sensors 20, sensor cables 22 may be separate or may be tied, combined, or otherwise joined together along at least a portion of their length. Embodiments of a delivery shaft 16, a deployment member 18, and a constrictor 14 having features of the invention are shown individually in FIGS. 2A, 2B and 2C respectively.

FIG. 2A is a perspective view of a delivery shaft 16 having a sensor 20 and a sensor cable 22. Delivery shaft 16 has a distal portion 30, a proximal portion 32, and a length 34. Delivery shaft 16 also has an outer diameter 36 and, in embodiments in which a delivery shaft 16 is hollow, or has an internal cavity forming at least a partial lumen, a delivery shaft 16 may also have an inner diameter 38. Tapered distal extensions 40 having distal tips 42 are configured to engage tissue and to apply pressure adjacent to the patient's cervix to tissue to occlude an underlying uterine artery. As shown in FIGS. 1 and 2A, sensors 20 may be disposed on distal extensions 40 of a delivery shaft 16, near or at distal tips 42, where they are disposed in a favorable position to sense blood flow in an artery when a delivery shaft 16 is in contact with tissue. A pair of sensors 20 are disposed on the delivery shafts 16 shown in FIGS. 1 and 2A. However, alternatively, a device 12 having features of the invention may have only a single sensor 20, or may have more than two sensors 20 disposed on a delivery shaft 16. A sensor 20 is preferably disposed at or near a distal extension tip 42; however a sensor 20 may be disposed at various suitable locations on a distal portion 30 of a delivery shaft 16 of a device 12. Alternatively, where at least one sensor 20 is disposed on a cervical constrictor 14, a delivery shaft 16 may have no sensor 20.

A deployment member 18 is shown in FIG. 2B and is preferably a cylindrical tube having an internal lumen 44 allowing passage of a delivery shaft 16 therethrough. The internal lumen 44 of the deployment member 18 has an inner diameter 46 that is greater than the outer diameter 36 of delivery shaft 16. Deployment member 18 also has an outer diameter 48 and a wall thickness 50. A deployment member 18 has a distal portion 52, a proximal portion 54 and a deployment member length 56.

A constrictor 14 is configured to apply pressure to tissue effective to compress and occlude an artery. For example, a constrictor 14 may be deployed onto or around a cervix so as to apply pressure to a cervix or uterus effective to occlude a uterine artery. An embodiment of a constrictor 14 having features of the invention that may be termed a wireform is shown in FIG. 2C. A wireform is a structure configured to engage tissue having a frame of elongated material, typically wire, tube, or ribbon. The elongated material may be bent or otherwise shaped to form a looped structure such as, for example, one of the structures shown in FIGS. 2C and 3A–3G. A wireform is configured to compress a cervix and uterine body when deployed from the delivery shaft 16, and is typically resilient (e.g., by being constructed of resilient material). A wireform may also have paddles or other features attached to, or formed from, its frame, that may be configured to engage or compress tissue. The example of a wireform having features of the invention shown in FIGS. 1 and 2C has a pair of pressure-applying members in the form of loops 60 having loop ends 62 and joined by a proximal connecting member 64. A wireform as shown in FIGS. 1 and 2C includes a pair of sensors 20 disposed on loop ends 62, and connected to sensor cables 22 having cable connectors 26. A constrictor 14 has a diameter or width 66, and a length 68 as shown by the example in FIG. 2C. In embodiments of a constrictor 14, the length of a loop 60 will be the constrictor length 68, and so length 68 may also be termed a loop length. The pressure-applying members of a wireform (loops 60 including loop ends 62) are configured to press into tissue, compressing it or distending it so as to occlude an underlying or adjacent artery or arteries.

Loops 60 are disposed in an expanded configuration when mounted on a delivery shaft 16. Tapered distal extensions 40 of delivery shaft 16 are configured to hold pressure-applying members (e.g., loops 60) in an expanded configuration suitable for placement around a cervix and onto a patient's uterus, and to allow the deployment of a tissue constrictor 14 as it is pushed forward by a deployment member 18. Following deployment onto a cervix and around the patient's uterine body, free from the internal restraint imposed by the tapered distal extensions 40 of delivery shaft 16, loops 60 assume a second, contracted pressure-applying configuration and apply pressure to the uterus, cervix and other tissue effective to occlude underlying or adjacent uterine arteries.

A location sensor 20 is effective to locate a uterine artery, to detect blood flow in a uterine artery, and to adjust the amount of force used in order to reduce or abolish blood flow in the artery. Two sensors 20 are shown disposed on constrictor loop ends 62 in FIG. 2C. In other embodiments, a constrictor 14, such as a wireform, may have one sensor 20, or more than two sensors 20; a sensor 20 or sensors 20 may be disposed at other positions on a constrictor 14. Sensors 20 may be disposed at other distal locations, such as on a delivery shaft 16 as illustrated in FIGS. 1 and 2A. In embodiments of devices having features of the invention, sensors 20 may be disposed on both a delivery shaft 16 and on a constrictor 14; on only a constrictor 14; or only on a delivery shaft 16.

A constrictor 14 having features of the invention may include a variety of mechanisms configured to engage and compress tissue so as to occlude an artery. Examples of several embodiments of constrictors 14 having features of the invention are shown in FIGS. 3A through 3G. It will be understood that the number of location sensors 20 shown in the Figures is not limiting, as a constrictor 14 may have no, one, or multiple location sensors 20.

A constrictor 14 is preferably formed of a suitable resilient material, such as spring steel or stainless steel, including heat-treated stainless steel, and including memory metals such as nickel titanium alloys (e.g., NITINOL). Alternatively, or in addition to a metal, a constrictor 14 may be made from resilient polymer, ceramic, elastic, rubber, or other material configured to apply sufficient pressure to at least partially occlude a uterine artery when a constrictor 14 is disposed in a pressure-applying configuration in contact with tissue. Biocompatible polymers, such as biocompatible and sterilizable thermoplastic and thermoset materials such as for example, polycarbonate, polysulfone, polyester, polyethylene, polyacetal, and other polymers may be particularly suitable for embodiments of the invention. Devices 12, including a constrictor 14, a delivery shaft 16 and a deployment member 18, are preferably made from biocompatible and sterilizable materials, and may be designed for single use (disposable) or may be sterilizable and capable of being used multiple times.

In alternative embodiments, a constrictor 14 may be constructed of deformable non-resilient materials. For example, a non-resilient constrictor 14 may be deployed by compressing or squeezing it onto tissue, deforming the constrictor 14 so as to leave the constrictor 14 in a compressing configuration exerting pressure on the tissue, effective to occlude an artery. In other embodiments, a constrictor 14 made from non-resilient materials may have hinges, slides or other features enabling it to assume a constricting configuration.

Figure 3A:
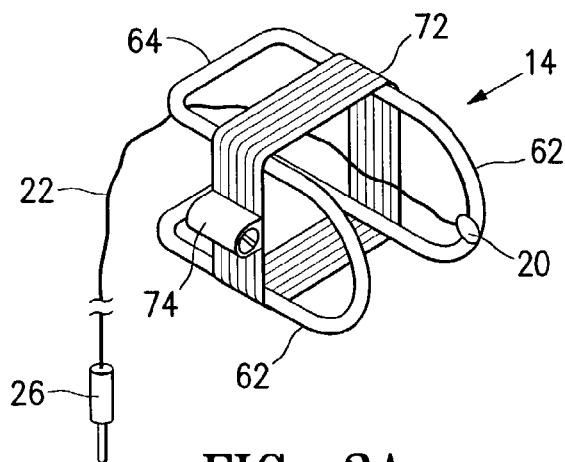
FIG. 3A is a perspective view of an alternative constrictor having features of the invention including a cinch.

Compressing force may be applied to or added to a constrictor 14 by additional elements. For example, as shown in FIG. 3A, a wireform may be circled by a cinch 72. A cinch 72 may be elastic and stretched around a portion of a wireform, so that the cinch is under tension and applies pressure to the wireform. A wireform with cinch 72 placed onto tissue is then effective to apply pressure to the tissue that is greater than the pressure that would be applied by the wireform alone. Cinch 72 may have a tightening mechanism 74, such as, for example, a rotating shaft configured to take up a portion of the cinch 72 onto a reel, or a screw with threads that fit into grooves, ridges or holes on the cinch 72 so that, when the screw is rotated, the cinch 72 tightens around the constrictor 14.

Figure 3B:
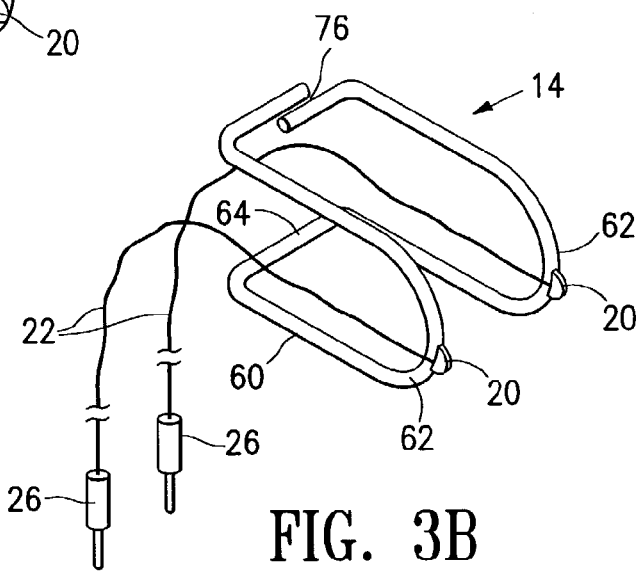
FIG. 3B is a perspective view of an alternative constrictor having features of the invention and having a gap on one of the loops.
Figure 3C:
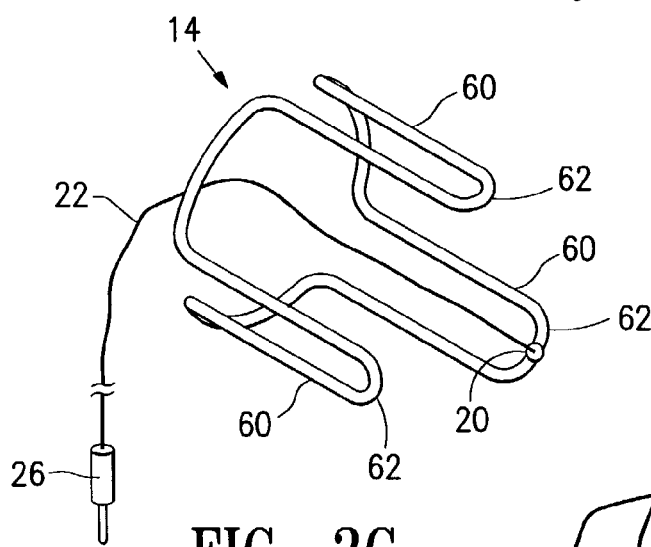
FIG. 3C is a perspective view of an alternative constrictor having features of the invention having three pressure-applying loops.

A wireform may be a continuous structure, as illustrated in FIGS. 1, 2C and 3A, for example. However, in other embodiments of constrictors 14, a wireform may have a gap 76 as illustrated in FIGS. 3B and 3F to provide for increased expansion of a wireform, above the amount of expansion possible in the absence of such a gap 76. Such expansion of a wireform may allow, for example, a smaller wireform to be carried by a delivery shaft 16 than would be otherwise possible. Where the wireform is a resilient wireform, a smaller wireform would be able to apply greater amounts of pressure to tissue, and to compress tissue to a greater extent, than would a larger wireform applied to the same tissue.

A wireform may have pressure-applying members that include multiple loops 60 with multiple loop ends 62. As shown in FIG. 3C, a wireform having features of the invention may have three loops 60. In other embodiments, a constrictor 14, such as a wireform, may have more than three pressure-applying loops 60.

Figure 3D:
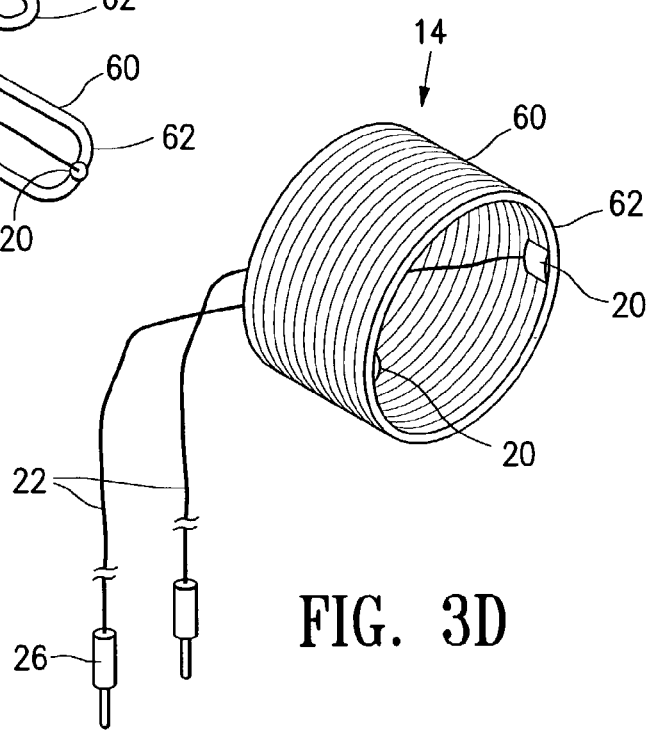
FIG. 3D is a perspective view of an alternative constrictor having features of the invention comprising a single loop configured to apply pressure to a cervix.

As illustrated in FIG. 3D, a constrictor 14 having features of the invention may be a single loop 60 of resilient material configured to apply pressure to tissue. Such a constrictor 14 may be made from a single band of elastic, rubber, or other resilient material; or may be a woven, braided, or other composite material including resilient and non-resilient components. A constrictor 14 having only a single loop 60 may have a gap 76, and may be made from metal (e.g., NITINOL or heat-treated stainless steel), polymer, or other material as well.

Figure 3E:
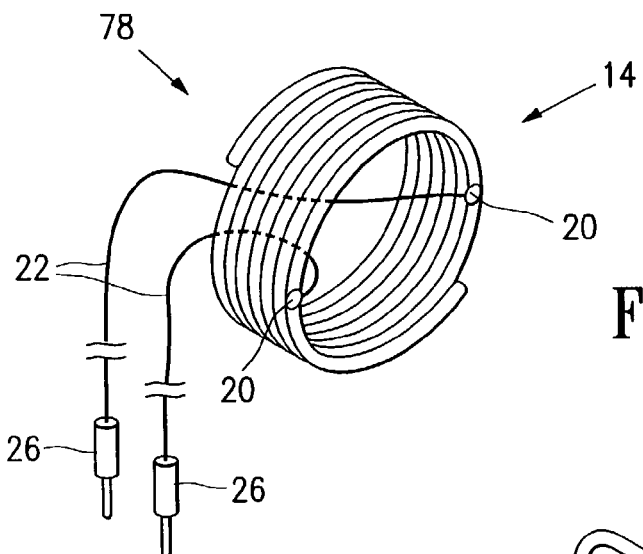
FIG. 3E is a perspective view of an alternative constrictor having features of the invention which is in the form of a coil of resilient material.
Figure 3F:
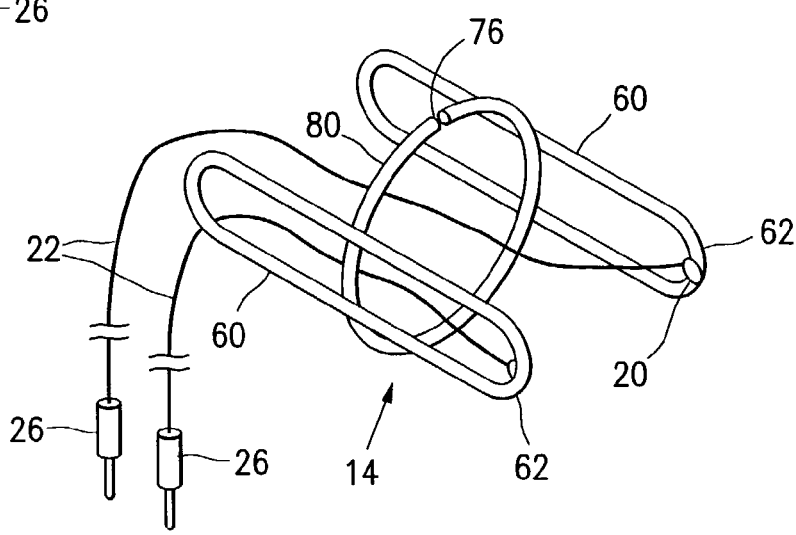
FIG. 3F is a perspective view of an alternative constrictor having features of the invention having a pair of pressure-applying loops attached to an equatorial loop.

A constrictor 14 may include a coil 78 of resilient material, as illustrated in the example shown in FIG. 3E. Such a coiled constrictor 14 may be expanded radially for mounting on a delivery shaft 16, and may contract radially upon deployment onto tissue, effective to compress the tissue and to occlude an artery. A constrictor 14 may also expand or contract in a longitudinal direction as well.

The wireform shown in FIG. 3F has a pair of pressure-applying loops 60 that are connected by a central connecting member 80. The central connecting member 80 and the loops 60 may have a gap 76 or gaps 76 as well, to allow or increase the expansion of the wireform when stretched (e.g., when mounted onto a delivery shaft 16). Such loops 60 may be effective to guide a wireform onto tissue, and to retain a wireform on tissue, after deployment, as well as to apply pressure to tissue.

Figure 3G:
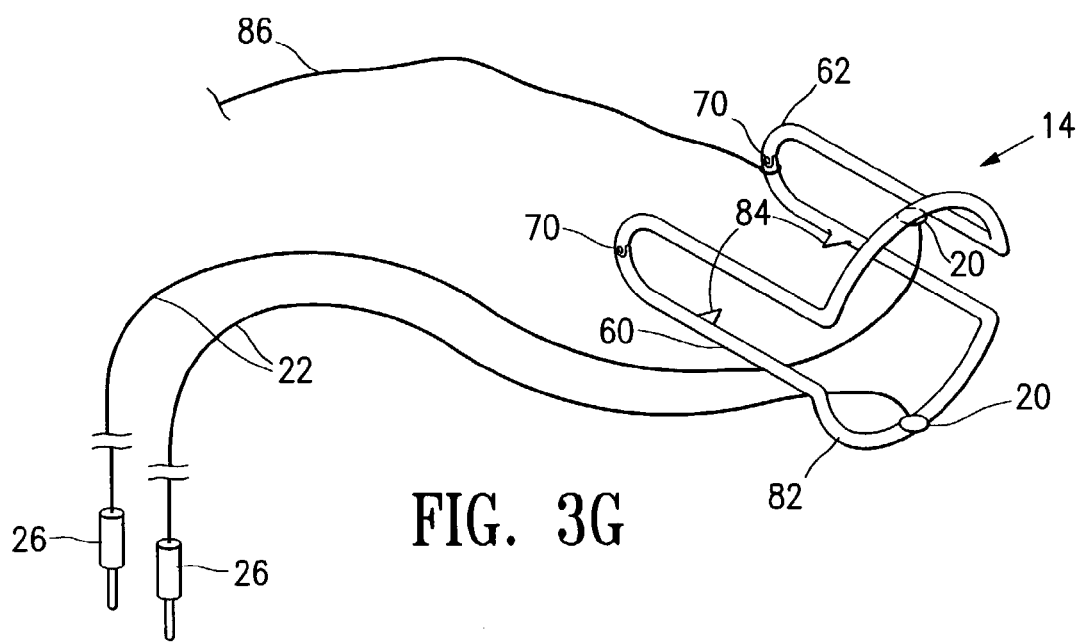
FIG. 3G is a perspective view of an alternative constrictor having features of the invention having a pair of pressure-applying loops with a distal connecting member, hinges, and a removal element.

Alternatively, as shown in FIG. 3G, a constrictor 14 having features of the invention may include a wireform which has a pair of pressure-applying loops 60 joined by a distal connecting member 82. A distal connecting member 82 may be configured to press onto or to press into tissue. After deployment of a constrictor 14, a distal connecting member 82 contacts tissue in approximately the same position and orientation as would loops 60 of a wireform as illustrated in FIGS. 2C, 3A, 3B, and 3F, for example. However, a distal connecting member 82 would contact a greater amount of tissue in that position and orientation than would loops 60 of a constrictor 14 having such loops 60 that was similarly positioned and oriented.

A wireform may also have a hinge or hinges 70 to allow for expansion of loops 60, as shown in FIG. 3G. A hinge 70 may be a passive hinge, allowing rotation in response to torque, or may include a spring or other restorative element configured to oppose opening torque so that, once opened and placed in contact with tissue, a wireform having a hinge 70 would apply pressure on tissue placed within loops 60. A hinge 70 may also have a lock or stop configured to restrict movement of the hinge when engaged.

In addition, as shown in FIG. 3G (although applicable in any constrictor 14 as illustrated in any of the figures, and in other embodiments as well), a wireform may have retaining elements 84 configured to engage tissue and to prevent inadvertent movement of a constrictor 14 after deployment. A retaining element 84 may be a tooth, a ridge, a depression, serration, a roughened surface, or other feature or member that is effective to help the constrictor 14 to firmly grip tissue. A delivery shaft 16 may have a slot 88 or other feature configured to accommodate a retaining element 84. Similarly, a lanyard 86, shown in FIG. 3G, may be used to aid in the removal and retrieval of a constrictor 14 after a desired period of tissue compression; a lanyard 86 may be used with any constrictor 14 shown in the figures and in other embodiments of a constrictor 14 as well.

The systems 10 and devices 12 are configured to place a sensor 20 and a constrictor 14 within a patient's body, which may be controlled from outside a patient's body, and to provide output from the sensor 20 located within a patient's body to a location outside a patient's body. A location sensor 20 (or location sensors 20) is preferably disposed on a wireform positioned effective to detect blood flow in a blood vessel when the wireform is near to or in contact with tissue having a blood vessel. A location sensor 20 may be integrated into a constrictor 14, e.g., molded into the constrictor 14 itself, or alternatively can be mounted on a constrictor 14. A location sensor 20 may be permanently mounted in or on a constrictor 14, or may be removably mounted in or on a constrictor 14. Preferably, a location sensor 20 disposed on a wireform is disposed at or near a loop end 62 on a pressure-applying loop 60.

The location sensor 20 for detecting a blood vessel may sense pulsation, blood flow, sound (including ultrasound), electromagnetic radiation (e.g., infra red radiation), pH, or other indicator which may be used to detect and/or locate a blood vessel. A sensor 20 may be disposed on a pressure-applying member 60 of a constrictor 14 and/or on a distal extension 40 of a delivery shaft 16 and may be configured to sense a blood vessel in a sensing direction which is preferably oriented substantially perpendicular to a tissue-contacting surface. In embodiments of devices having features of the invention a sensor having a sensing direction may assume other orientations (e.g., a sensing direction oriented substantially parallel to a pressure-applying member).

Preferably, a location sensor 20 is a Doppler ultrasound sensor, configured to emit and to detect ultrasound signals effective to detect blood flow and to locate a blood vessel. Ultrasound reflected from moving blood cells exhibits a Doppler frequency shift that can be measured by the transceiver electronics and sent to a speaker to create an audible signal corresponding to the velocity of the moving blood cells. Doppler ultrasound systems typically include a sensor controller 24 configured to receive information from a sensor 20, and which may also provide power or signals to a sensor 20, a signal output, and may control the operation of the sensor 20. For example, a sensor controller 24 may include an electrical connector to plug in the sensor, a power switch to power-on the transceiver electronics, an audible speaker output so that an operator can hear the Doppler frequency shift, a volume adjustment to control overall sound level, and batteries or other power source to provide energy which aids a piezoelectric ultrasound sensor to produce and to detect ultrasound energy.

Commercially available Doppler ultrasound sensors and sensor systems suitable for use in the present invention include the Koven model ES 100X MiniDop VRP-8 probe (St. Louis, Mo.), the DWL/Neuro Scan Medical Systems' Multi-Dop B+ system (Sterling, Va.), and the MedaSonics® CardioBeat® Blood Flow Doppler with Integrated Speaker (Cooper Surgical, Inc., Trumbull Conn. 06611)).

A location sensor 20 may be operatively connected to a sensor controller 24 by a sensor cable 22. A sensor controller 24 may connect with a single sensor 20, or with multiple sensors 20. A connector 26 is preferably a reversible connector configured to readily engage and disengage with a sensor controller 24. Alternatively, a cable 22 may directly and permanently engage a sensor controller 24 without having a connector 26 (e.g., may be soldered, brazed, welded, secured by a screw, or otherwise securely connected). A cable 22 connecting sensor 20 with a sensor controller 24 may include an electrical cable, an optical fiber, a waveguide, other conduit for carrying energy or signals, or a combination of these.

Ultrasound frequencies suitable for use with a location sensor 20 that is a Doppler ultrasound sensor include frequencies between about 5 Megahertz (MHz) and about 20 MHz, preferably between about 6 MHz and about 10 MHz, more preferably about 8 MHz. A location sensor 20 may also be, for example, an infrared or other electromagnetic energy sensor. Electromagnetic energy useful for sensing a location of a blood vessel or of blood flow in a blood vessel may have a wavelength of between about 500 nanometers (nm) and about 2000 nm, preferably between about 700 nm and about 1000 nm.

A sensor 20 is preferably mounted on a pressure-applying member of a constrictor 14, such as a loop 60, preferably at or near the distal tip, such as a loop end 62. A sensor 20 may have a preferred direction from which signals may be received; the preferred direction may be perpendicular, parallel, or at another angle to a surface in or on which the sensor 20 is located. Thus, a sensor 20 preferably has a sensing direction, in which a blood vessel that is located along a sensing direction is detectable by the sensor 20. A sensing direction is defined with respect to a sensor 20, and typically includes a range of directions, such as a range of directions within a solid angle taken with respect to a pressure-applying loop 60 of a constrictor 14 in or on which a sensor 20 is disposed, effective that a blood vessel disposed at least in part in or across the solid angle of a sensing direction is detectable by a sensor 20. Thus, a sensor 20 may be configured to indicate the location of a blood vessel with respect to a constrictor 14. A sensor 20 is typically disposed on or within a pressure-applying member 60 so that its sensing direction is substantially parallel to the length of a pressure-applying member of a constrictor 14. Such a sensing direction is effective to locate blood vessels or detect blood flow in arteries near a constrictor 14. A sensing direction that is substantially parallel to a pressure-applying member, along a length 68 of loop 60, may include directions from a sensor 20 within a solid angle of between about −30° and about 30° with respect to length 68. However, other sensing directions are also suitable, including, for example, sensing directions that are substantially perpendicular to a pressure-applying member, within a solid angle of between about 70° and about 110° with respect to length 68.

In embodiments of the invention, it may be advantageous to provide only one, or only a few, sensors 20 (e.g., one or a few Doppler ultrasound crystals) for sensing blood flow. A limited number of sensors 20 provides information that may be simply interpreted and evaluated. For example, the output of a single Doppler ultrasound crystal may be directed to a sound system to provide an audible signal to be monitored by the operator of the system 10. A change in the frequency of the audible signal or in another audible characteristic of the signal, is useful to identify the presence of a blood vessel in tissue near the sensor, and is typically readily understood by an operator. Alternatively, a plurality of Doppler ultrasound crystals may be advantageous in providing more data about the flow of blood through an artery of interest than would be available from a single sensor 20. It will be understood that the additional data derived from multiple sensors 20 may require additional manipulation that can increase the complexity and cost of the device.

To detect blood flow in the uterine arteries, ultrasound transducers may be placed within a vagina. Ultrasound transducers may, for example, point axially into the patient's tissue and insonate it to a depth of typically 2 cm (attenuated through tissue) for 8 MHz systems. The bilateral uterine arteries run laterally inward from sidewall of pelvis to the uterus just behind the vaginal mucosa near the cervix, and are by far the single largest blood vessels in this area, making their detection by ultrasound relatively straightforward. In addition, the inventors have discovered that a Doppler crystal may be optimized for uterine vessel detection by configuring it to detect blood flow in a wide region detected by the sensors.

Figure 4A:
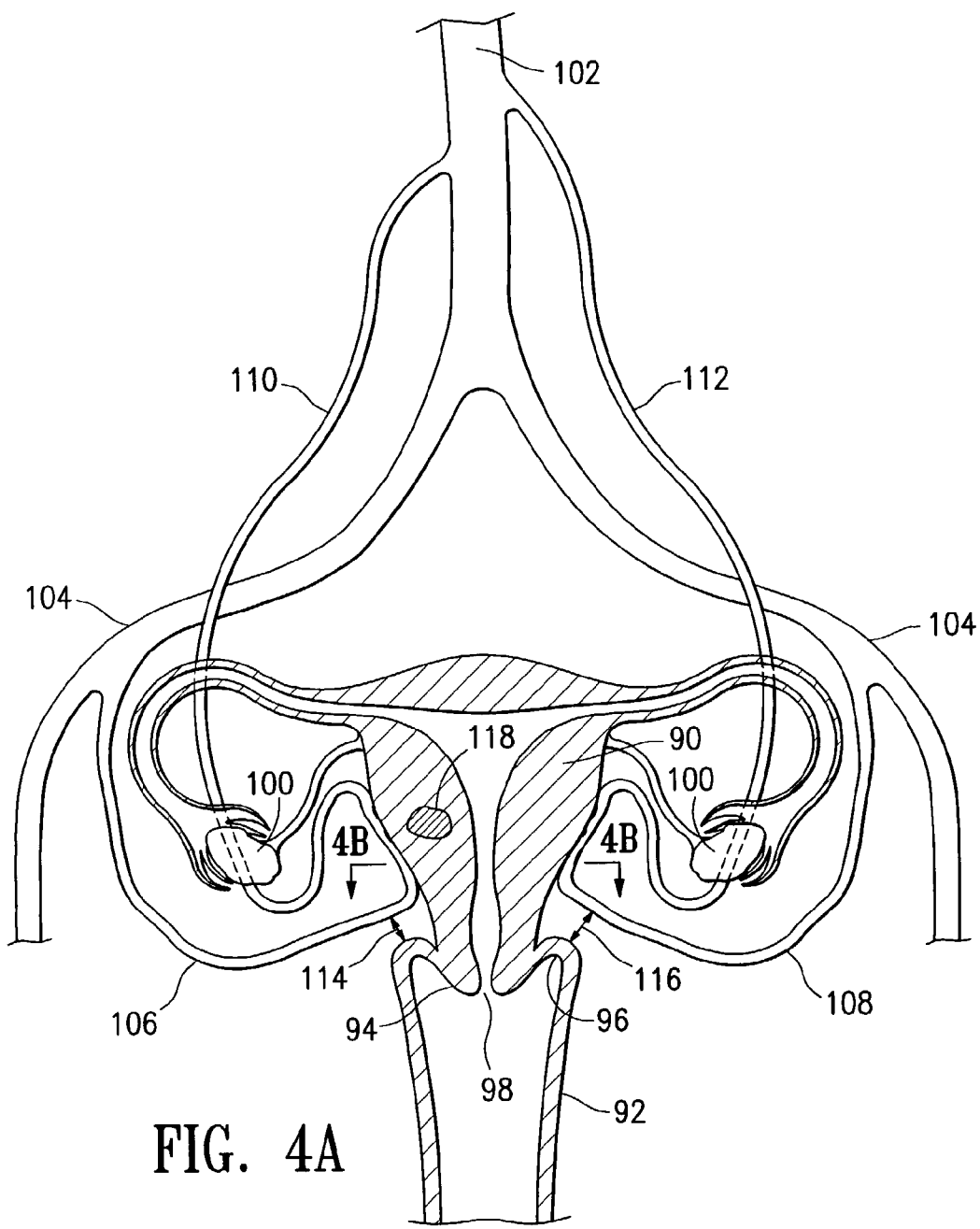
FIG. 4A is a schematic diagram of a reproductive system of a human female including major blood vessels providing blood flow to the uterus, shown in a coronal sectional view.

A schematic diagram of female human reproductive anatomy and related structures is shown in FIG. 4A. Uterus 90 may be accessed via vagina 92 and cervix 94. A vagina 92 has a wall extending to form the vaginal fornix 96 adjacent cervix 94. Cervix 94 may be approached by medical instruments such as a system 10 having features of the invention. Cervical os 98, located at the apex of the cervix 94, provides an opening into the uterus 90. Ovaries 100 are also shown in FIG. 4A. The blood supply to the uterus derives from the aorta 102 and the iliac arteries 104, with right uterine artery 106 and left uterine artery 108 branching off the iliac arteries 104, while right ovarian artery 110 and left ovarian artery 112 branch from the aorta 102. As illustrated in FIG. 4A, the uterus 90 thus has at least two sources of blood supply: the uterine arteries 106 and 108, and the ovarian arteries 110 and 112. It is believed that, in most women, the uterine arteries provide the more significant fraction of the uterine blood supply.

Figure 4B:
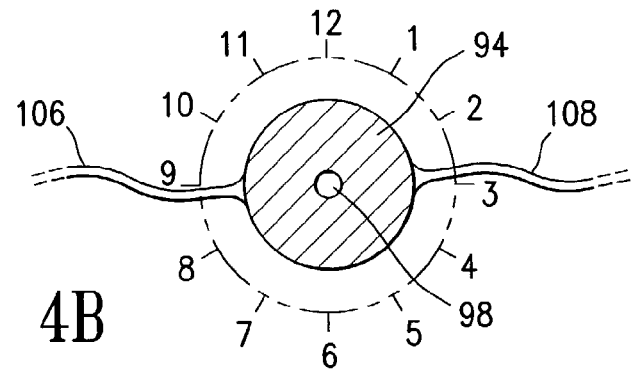
FIG. 4B is a schematic diagram of a reproductive system of a human female taken along the line 4B—4B of FIG. 4A.

The positions of the uterine arteries 106 and 108 with respect to the uterus 90 will be described in terms of a clock face, i.e., the positions of the uterine arteries will be identified as corresponding to particular times on a clock. A clock face is superimposed onto a schematic diagram showing the uterus 90 and uterine arteries 106 and 108 in FIG. 4B. In this context, 12 o'clock is the anterior direction from the center of the cervical os 98, 6 o'clock is posterior therefrom, 3 o'clock is laterally to the right (the patient's left side, see FIG. 4B), and 9 o'clock is laterally to the left (the patient's right side, see FIG. 4B). As will be readily apparent to those of skill in the art, the use of the clock face as a reference frame is used merely to simplify the discussions herein, and other reference frames, such as degrees or radians from a known or ascertainable reference line, can be interchangeably used herein.

The uterine arteries of female humans are typically disposed about 3 cm or less from the vaginal wall near the vaginal fornix 96 where a uterine artery 106 or 108 meets the uterus 90, although the uterine arteries for a single patient sometimes are spaced at slightly different distances 114 and 116 between the right uterine artery 106 and the vaginal fornix 96 (distance 114) and between left uterine artery 108 and vaginal fornix 96 (distance 116) (see FIG. 4A). The left uterine artery 108 is typically disposed at a position between about the 1 and 5 o'clock (see FIG. 4B) positions, and more frequently between about 2 and 4 o'clock. There is typically symmetry between the uterine arteries, i.e., the right uterine artery 106 is typically disposed at a position between about the 7 and 11 o'clock positions, and more frequently between about 8 and 10 o'clock. The cervix 94 can be used as a platform and a landmark from which to locate and access a uterine artery 106 or 108 because of the axial symmetry of the cervix 94 and its generally cylindrical or frustoconical exterior shape. Furthermore, the uterus 90, because it is a muscular and generally firm mass which resists deformation more than its adjacent tissues, including the uterine arteries 106 and 108, can be used as a backstop or anvil against which a uterine artery 106 or 108 can be compressed. See also U.S. application Ser. No. 09/908,815, filed Jul. 20, 2001, to Fred Burbank et al. ("'815 application"), co-assigned with the present application, the entire contents of which are incorporated by reference herein, for additional discussions of the anatomy of the uterus, cervix, and vaginal wall. Compression of uterine arteries 106 and 108 by compressing them against a uterus 90, leading to occlusion of these arteries, may be effective to treat a fibroid 118 or other uterine conditions requiring treatment.

A constrictor 14, delivery shaft 16, deployment member 18, and other elements and devices 12 of a system 10 are preferably configured for use in occluding one or both of the uterine arteries 106 and 108 of a female human patient. Thus, for example, a constrictor 14 is preferably configured to engage a cervix 94 and uterine body 90, to apply pressure to tissue such as a uterus 90, cervix 94 or vaginal fornix 96, effective to compress and occlude a uterine artery 106 or 108. Distal extensions 40, including distal tips 42, of a delivery shaft 16 are preferably configured to engage the cervix 94, and to press into the vaginal fornix 96, of a female human patient. As shown in FIGS. 1 and 2A, sensors 20 may be disposed on distal extensions 40 of a delivery shaft 16, near or at distal tips 42, where they are disposed in a favorable position to sense blood flow in a uterine artery 106 or 108 when a delivery shaft 16 is pressed into a vaginal fornix 96 within a vagina 92. The pressure-applying members 60 of a constrictor 14, including loop ends 62, are configured to press onto a cervix 94 or into a vaginal fornix 96, compressing a cervix 94 or distending a vaginal fornix 96 and applying pressure to a uterus 90 or cervix 94 so as to occlude one or both uterine arteries 106 and 108.

Figure 5A:
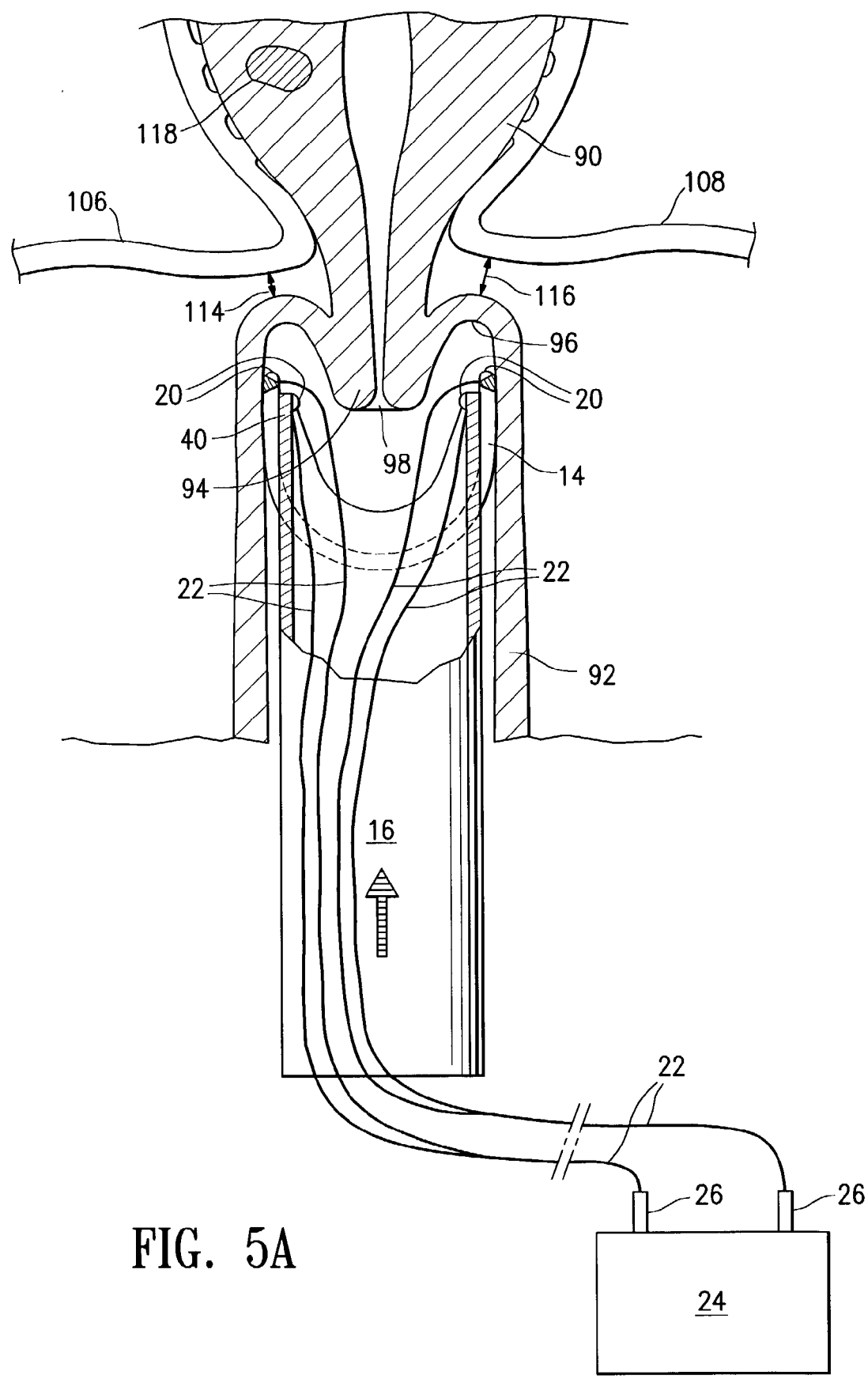
FIG. 5A includes a schematic diagram of a portion of the reproductive anatomy of a human female, showing a delivery shaft carrying a constrictor beginning to apply the constrictor to the cervix.

In FIG. 5A, a distal portion 30 of a delivery shaft 16 carrying a constrictor 14 is introduced into a vagina 92 of a female patient having a uterine fibroid 118 on or within her uterus 90. The delivery shaft 16 is oriented so that distal extensions 40 of the delivery shaft 16 contact and then press into the vaginal fornix 96 near to the uterine arteries 106 and 108 as the delivery shaft 16 is inserted to increasing depth within vagina 92.

Figure 5B:
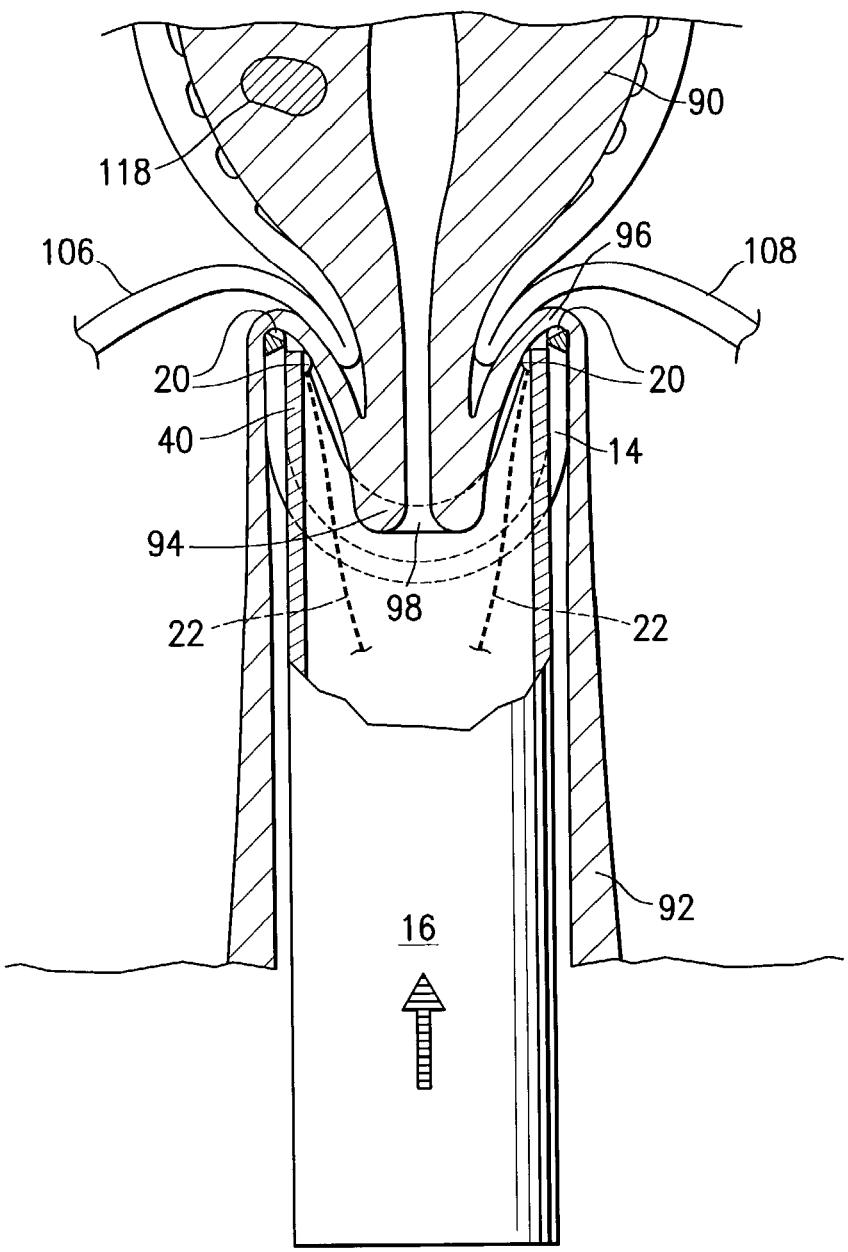
FIG. 5B includes a schematic diagram of a portion of the reproductive anatomy of a human female, showing a distal portion of a delivery shaft carrying a constrictor pressing into the vaginal fornix and beginning to occlude the uterine arteries.
Figure 5C:
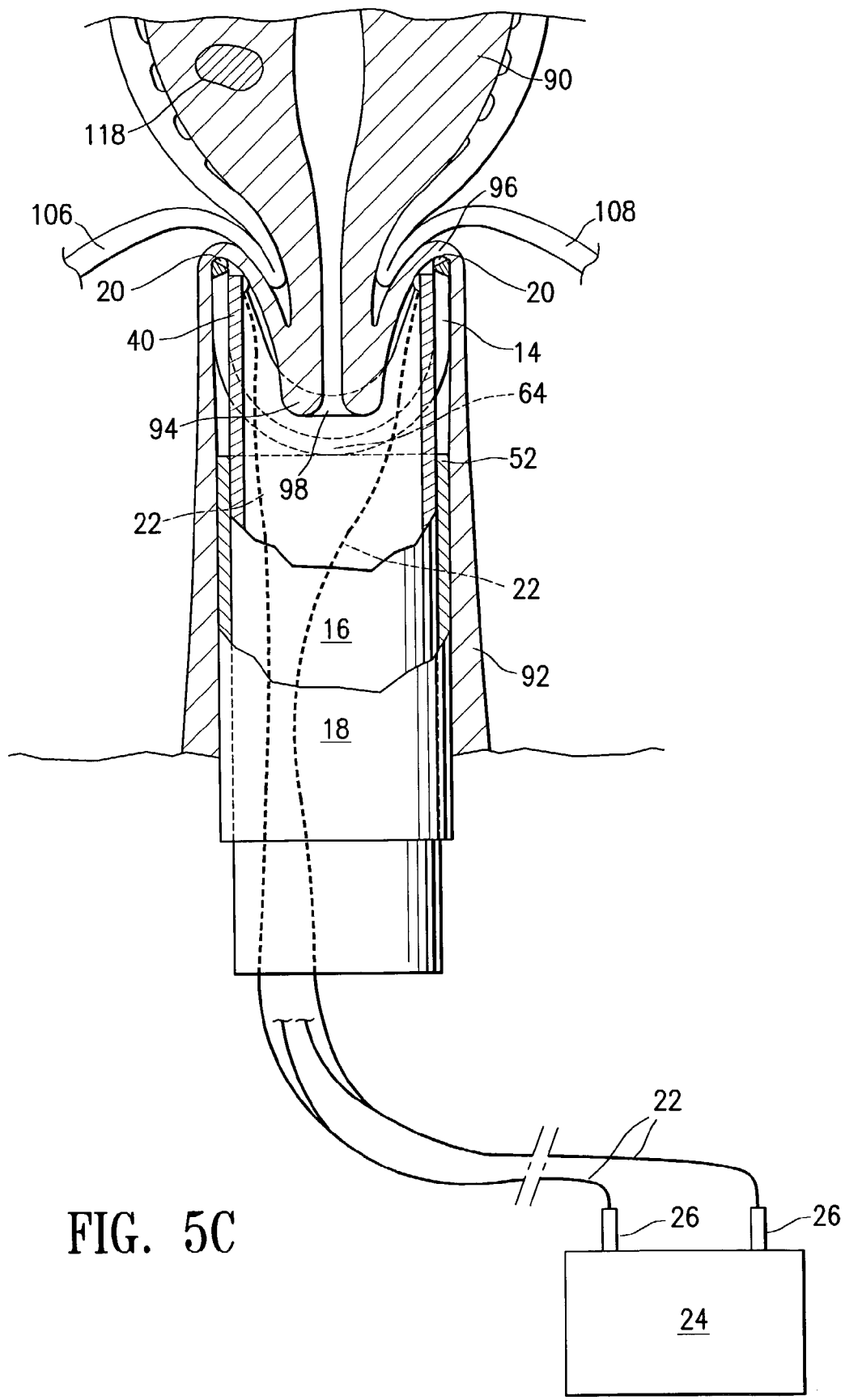
FIG. 5C includes a schematic diagram of a portion of the reproductive anatomy of a human female, showing a deployment member pressing on a proximal portion of the constrictor to deploy the constrictor onto the cervix.
Figure 5D:
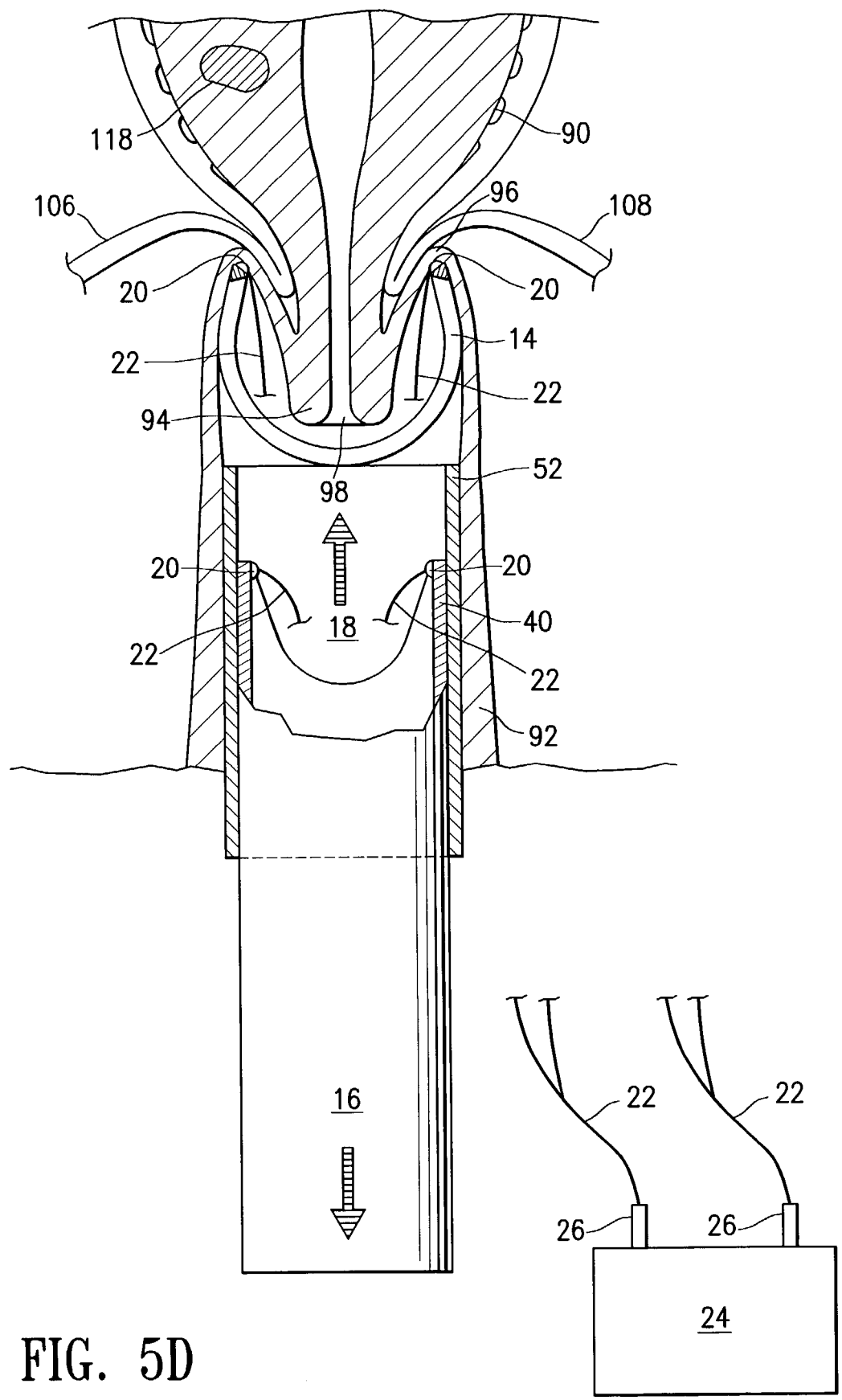
FIG. 5D includes a schematic diagram of a portion of the reproductive anatomy of a human female, showing removal of the delivery shaft after the constrictor has been placed onto the cervix.

As shown in FIG. 5B, pressure from the delivery shaft 16, and particularly from extensions 40, stretches and distends vaginal fornix 96. The arrow shown in FIG. 5B indicates the direction of pressure applied on the delivery shaft 16 and thus to the patient's tissue as shown. Introduction of the delivery shaft 16 into vagina 92, and the resulting pressure and distension of tissue, moves uterine arteries 106 and 108 so that they more closely approach uterus 90, and become compressed between uterus 90 and vaginal fornix 96. Note that distances 114 and 116 shown in FIG. 5A are reduced by the distension of tissue, so that, as shown in FIGS. 5B–5D, distances 114 and 116 become zero. The pressure and tissue deformation resulting from the constrictor 14 pressing into the vagina 92 on or around cervix 94 towards the uterus 90 and vaginal fornix 96 may be effective to occlude the uterine arteries 106 and 108 as shown in FIG. 5B.

A reduction of blood flow in the uterine arteries 106 and 108 may be detected by sensors 20, and sensor signals carried by sensor cables 22 to sensor controller 24 that indicates to an operator the presence or absence, or the amount of, blood flow in a uterine artery. After uterine arteries 106 and 108 have been detected, the constrictor 14 may be deployed. In preferred methods of the invention, constrictor 14 is deployed after a reduction in blood flow in the uterine arteries 106 and 108 is detected.

A deployment member 18 is shown disposed around delivery shaft 16 and contacting the constrictor 14 in FIG. 5C. As shown in FIG. 5D, distal motion of the deployment member 18 (indicated by the pair of arrows to the left and to the right of deployment member 18 in FIG. 5D) is effective to push constrictor 14 distally and into place on cervix 94. Similarly, proximal motion of the delivery shaft 16 (indicated by the arrow within delivery shaft 16 in FIG. 5D) while deployment member 18 is positioned in contact with a proximal portion (e.g., proximal connecting member 64) of constrictor 14 is effective to deploy constrictor 14 into place on cervix 94. In preferred embodiments, both distal motion of deployment member 18, and proximal motion of delivery shaft 16, may be used to deploy a constrictor 14 into place on a cervix 94. Care should be taken that proximal motion of delivery shaft 16 does not relieve pressure on tissue so that occlusion of uterine arteries 106 and 108 is relieved or is insufficient.

Sufficient pressure and compression is effective to completely occlude a blood vessel located within compressed tissue, and thereby to abolish blood flow within the blood vessel. Temporary compression does not typically lead to irreversible damage or occlusion to the blood vessel; thus, upon release of the compression, blood flow returns to normal. An effective amount of pressure, suitable for occluding a blood vessel by compressing a blood vessel or tissue adjacent a blood vessel, is typically between about 3 pounds per square inch (psi) and about 200 psi, more typically between about 5 psi and about 80 psi, and may be between about 7 psi and about 10 psi. A constrictor 14 having features of the invention may produce pressures of between about 3 psi and about 200 psi, preferably between about 5 psi to about 80 psi, more preferably between about 7 psi and about 10 psi.

It may be preferred to manipulate or stabilize a cervix 94 before or during placement of a constrictor 14. A device suitable for manipulating or stabilizing the position of a cervix 94 and for producing tension in a cervix 94 and a vaginal fornix 96 is a tenaculum 120. Embodiments of tenacula are described in the co-pending U.S. patent application "Tenaculum for Use with Occlusion Devices" by Fred H. Burbank et al., assigned to Vascular Control Systems, Inc., filed on the same day as the present application, the disclosure of which is hereby incorporated by reference in its entirety. A tenaculum 120 may be used to provide a stable foundation for the use of other devices 12 and systems 10 for the occlusion of uterine arteries 106 and 108. For example, a tenaculum 120 may be used to guide the delivery shaft 16 within the vagina 92 to place a constrictor 14 onto the cervix 94, and may be used to manipulate the cervix 94, to reposition it or to apply tension to it during initial placement of the constrictor 14 and, if desired, for the duration of the occlusion of uterine arteries 106 and 108. A tenaculum 120 is shown in use in FIGS. 6A through 6C. Other suitable guides include guidewires and other similar instruments.

Figure 6A:
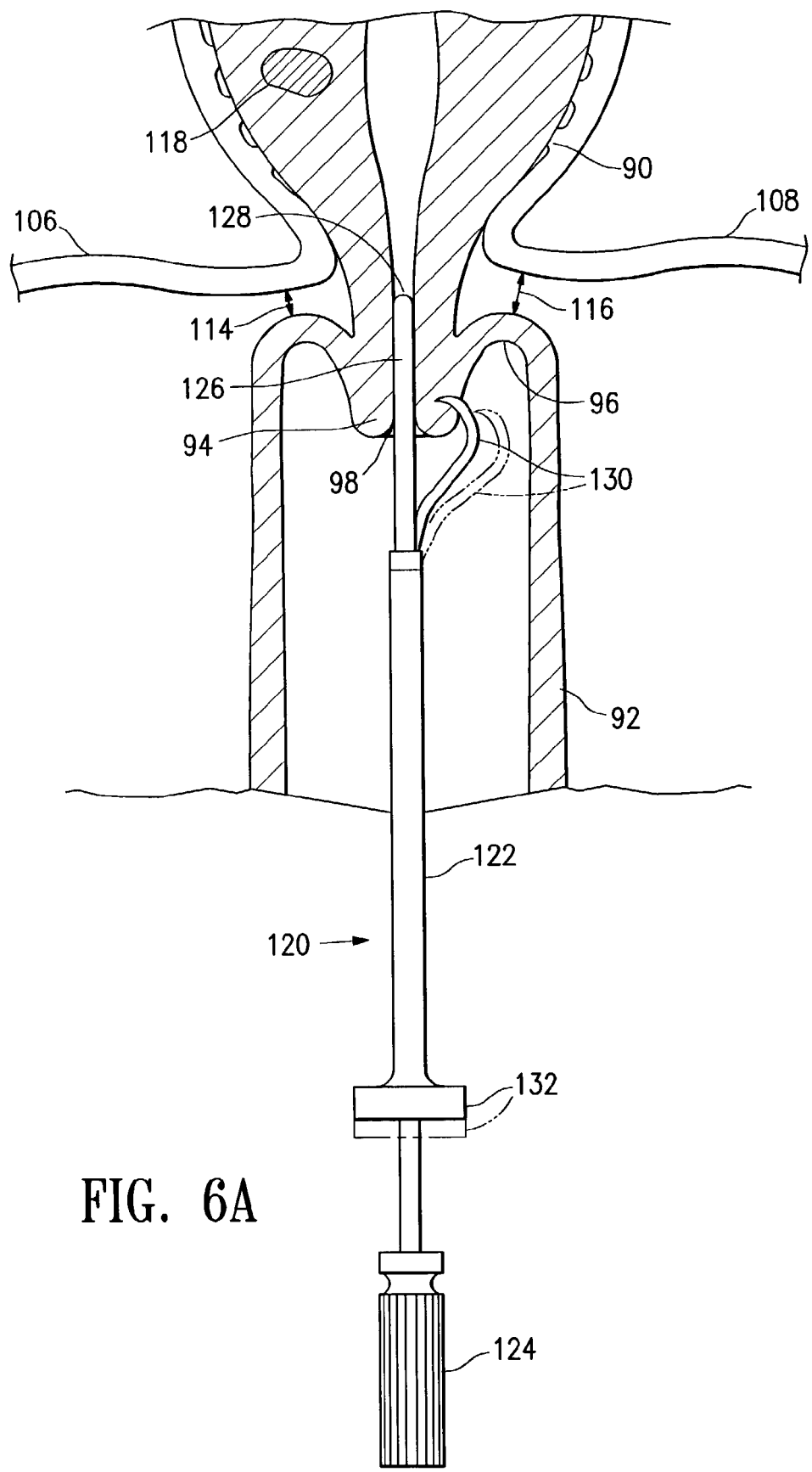
FIG. 6A includes a schematic diagram of a portion of the reproductive anatomy of a human female, showing a tenaculum with tenaculum sound in place within the cervical os and tenaculum spike engaged with the exterior of the cervix.

As shown in FIG. 6A, a tenaculum shaft 122 with handle 124 may be used to guide a tenaculum sound 126 as it is placed within a vagina 92. A sound 126 may be malleable or flexible in order to accommodate a patient's anatomy, including orientation and disposition of a patient's cervical os. Distal tip 128 of sound 126 is preferably rounded in order to reduce the possibility of trauma to the cervix and to reduce possible discomfort to the patient. Distal tip 128 of tenaculum sound 126 may be inserted without trauma into the cervical os 98, providing a structure for guiding subsequent placement of a device 12 of a system 10. A tenaculum 120 may be secured to the patient's uterus 90 by application of tenaculum spike 130 into tissue (typically a cervix 94, as shown in FIG. 6A) so as to retain tenaculum 120 in place. A spike 130 may be deployed, for example, by a spike controller 132 which may slide distally along a portion of handle 124 causing spike 130 to more radially inwardly and to engage tissue near to sound 126. A spike 130 may be disposed on a flexible arm that is fixedly attached to a shaft 122; may be disposed on a less flexible or rigid arm that is pivotally attached to a shaft 122; or may be otherwise movably connected to a shaft 122. A tenaculum 120 may include multiple spikes 130, and that other retention elements configured to retain a tenaculum 120 in place within or on a patient's body may be used with or in place of a spike 130.

Figure 6B:
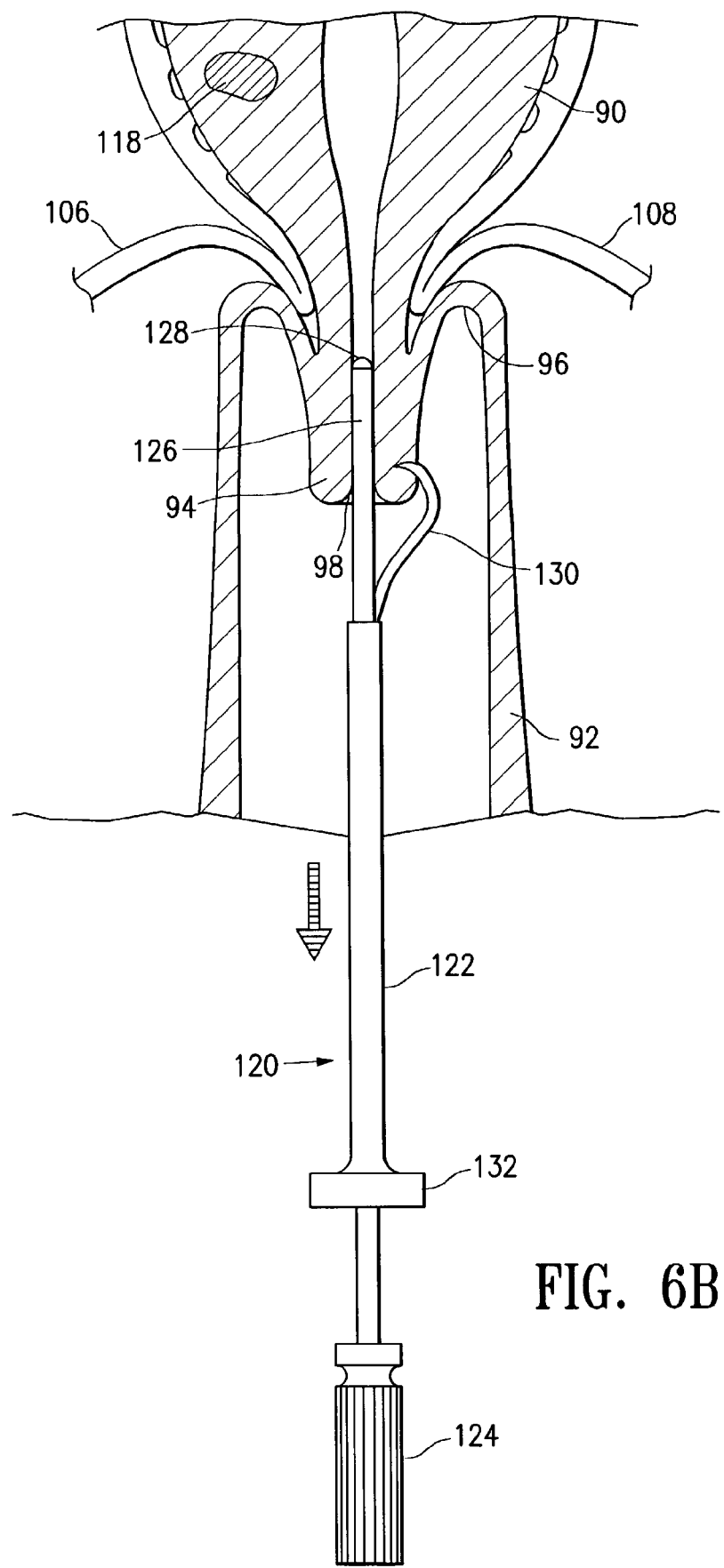
FIG. 6B shows the female reproductive anatomy and tenaculum shown in FIG. 6A, after tension has been applied to the cervix with the tenaculum so as to stretch the cervix and position the uterine arteries for occlusion.

A spike 130, or other retaining element, allows an operator to pull on or otherwise manipulate a patient's tissue with a tenaculum 120. Such manipulation of a patient's tissue may be desirable to place the tissue in a desired position or orientation; for example, pulling on a cervix 94 extends the cervix 94 and stretches adjacent tissue, such as the vaginal fornix 96, so as to provide a better configuration for placement of a constrictor 14 and for occlusion of uterine arteries 106 and 108. Pulling on tenaculum 120 secured to a cervix 94 with spike 130, as shown in FIG. 6B, stretches cervix 94 and vaginal fornix 96, and pulls uterine arteries 106 and 108 towards vagina 92 so that the arteries become stretched and compressed between vaginal fornix 96 and uterus 90.

Figure 6C:
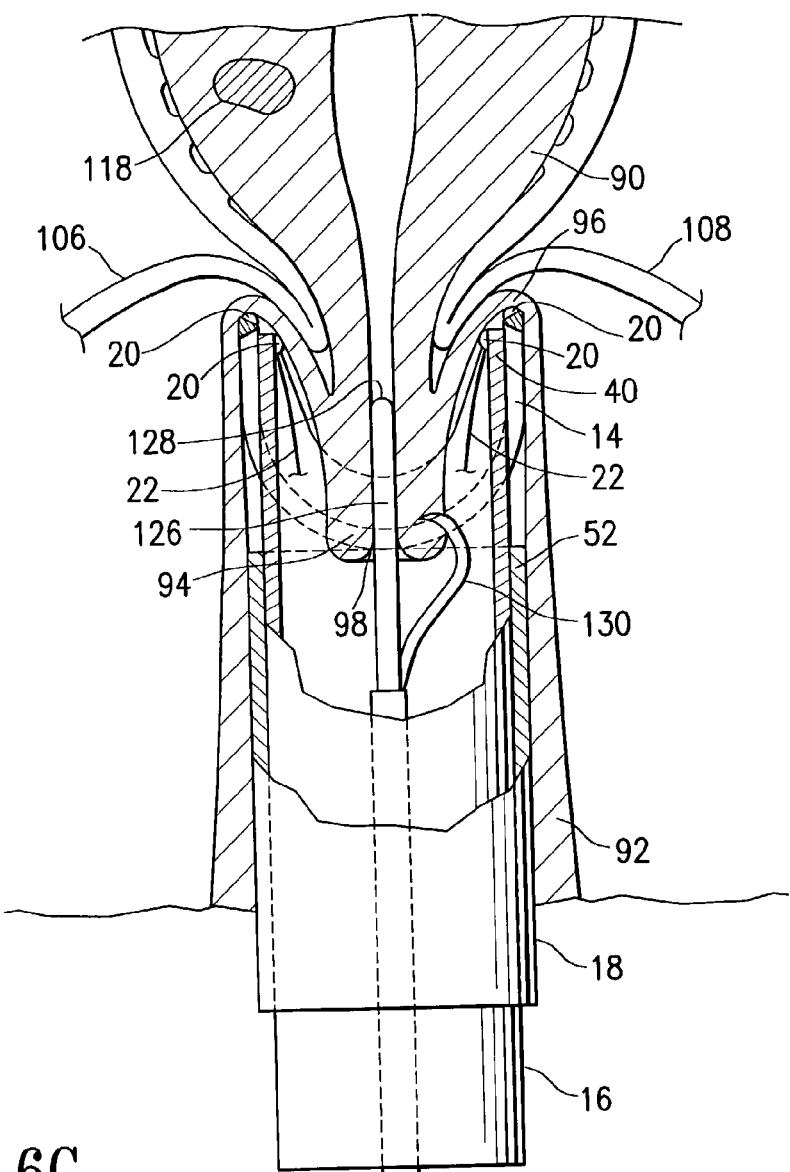
FIG. 6C shows the female reproductive anatomy and tenaculum shown in FIG. 6B, with a constrictor embodying features of the invention being delivered onto the cervix by a delivery shaft and deployment member.
Figure 6C:
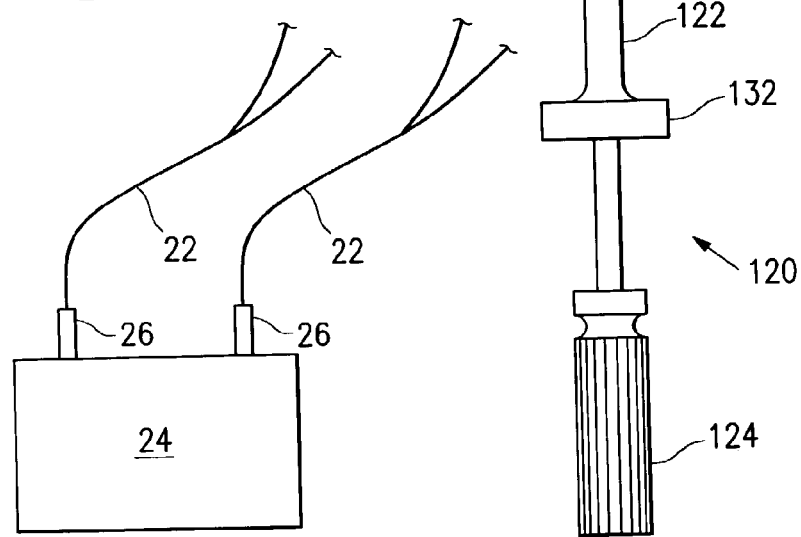

A delivery shaft 16 with constrictor 14 and deployment member 18 may be used in concert with a tenaculum 120. A delivery shaft 16 may be configured to deliver a constrictor 14 over a tenaculum 120 by, for example, having an inner lumen with an inner diameter 38 large enough to accommodate a tenaculum 120. FIG. 6C shows a tenaculum 120 applying tension to cervix 94 of a female patient at the same time that a delivery shaft 16, constrictor 14, and deployment member 18 are disposed within the patient's vagina. Tension applied by tenaculum 120 may be useful in deploying a constrictor 14 by, for example, placing cervix 94, vaginal fornix 96 and uterine arteries 106 and 108 into favorable positions for occlusion by a constrictor 14. Although spike 130 is shown engaging a lateral portion of a cervix 94 in FIGS. 6A–6C, in some cases it may be preferred that spike 130 engage a more anterior (e.g., nearer 12 o'clock) or posterior (e.g., nearer 6 o'clock) portion of a cervix 94 (for example, to insure that spike 130 does not interfere with or block placement of a sensor 20 or other element of a constrictor 14 or of a delivery shaft 16).

Recovery of a constrictor 14 may be effected or aided by pulling on a lanyard 86; in embodiments of the invention, a lanyard 86 may serve, at least in part, as a mechanism for the release of compression by a constrictor 14. For example, a constrictor 14 may be configured to release compression upon pulling of a lanyard 86 by having a pin or snap connected to a lanyard 86, so that pulling on the lanyard pulls a pin or snap from a lodgment, allowing expansion of at least a portion of the constrictor 14 so as to release compression on tissue, relieve occlusion of an artery, and allow recovery of the constrictor 14. A proximal connecting member 64, a loop, or other portion of a constrictor 14 may be cut or otherwise allowed to separate, allowing for its removal.

In further embodiments of the invention, a constrictor 14 and/or delivery shaft 16 may be configured for retrieval by reapplication of a delivery shaft 16 or other similar instrument. For example, a constrictor 14 may be recovered by pressing a delivery shaft 16 having a tapered distal portion 42 configured to slide between a constrictor 14 and tissue to which it is attached, expanding the constrictor 14 and lifting it away from and off of tissue. For example, a wireform made of material having a substantially triangular cross-section, as shown in FIGS. 5A–5D, may be configured to accept a distal wedge portion of a delivery shaft. Thus, a constrictor 14 may be remounted onto a delivery shaft 16 and then removed from a cervix 94 or other tissue onto which the constrictor 14 has been placed. Application of tension to a lanyard 86 during such a retrieval operation may aid in the recovery of the constrictor 14 by preventing its being pushed further distally onto tissue as a delivery shaft 16 is pressed underneath the constrictor 14.

A reduction or cessation of blood flow in a uterine artery may be observed with a sensor 20 for a therapeutically effective period of time, after which time a practitioner can release the compression from the uterine artery. As used herein, the term therapeutically effective time and its equivalents are used as in U.S. patent application Ser. No. 09/556,934, filed Apr. 21, 2000, by Burbank et al., and U.S. patent application Ser. No. 09/908,815, filed Jul. 20, 2001, by Burbank et al., both of which references are hereby incorporated by reference herein.

Accordingly, methods embodying features of the invention may also further comprise releasing pressure from the cervix 94. Such relief of pressure from a cervix 94 may include removal of a constrictor 14, release of compression by a constrictor 14 remaining in place on a cervix 94, or both, so that occlusion of a uterine artery is of a limited duration and lasts for only a limited time. In preferred methods, a uterine artery remains occluded for only a limited time. A suitable limited time may be between about 0.5 hours and about 24 hours, or preferably between about 1 hours and about 9 hours.

A wireform may be made from elongated material, such as a tubular material, having a transverse dimension configured to provide sufficient strength (and resiliency where the constrictor 14 is a resilient constrictor 14) to provide the desired pressure to tissue, and provide sufficient surface area so as to disperse the pressure on tissue sufficiently to avoid damage to tissue under compression. A wireform may be made of a single piece of tube and is preferably heat treated, resulting in a roughly triangular or rectangular cross-section (e.g., a triangular cross-section is shown in FIGS. 5A–5D). However, a wireform may have a circular cross-section, or other cross-sectional shape. In alternative embodiments, a wireform may be welded, glued or otherwise assembled from more than one piece of material. Preferably, a wireform is made from a material having a cross-sectional dimension of between about 0.02 inches and about 0.3 inches, preferably between about 0.03 and about 0.2 inches, more preferably between about 0.04 inches and about 0.125 inches.

Devices 12 of a system 10, including a constrictor 14, a delivery shaft 16, and a deployment member 18, are preferably sized and configured for use within a vagina 92 of a female human patient. Thus, according to particularly preferred embodiments, a delivery shaft length 34 may be between about 4 inches and about 18 inches, and is preferably between about 6 inches and about 12 inches. A delivery shaft outer diameter 36 may be between about 1 inch and about 4 inches in diameter, and is preferably between about 1.25 inch and about 3 inches in diameter. A delivery shaft inner diameter 38 is preferably sized to accommodate a tenaculum 120, and may be between about 0.9 inches and about 3.9 inches in diameter, preferably between about 1 inch and about 3 inches. A delivery shaft may have any suitable wall thickness, which may preferably be between about 0.06 inches and about 0.13 inches. A delivery shaft distal extension 40 is preferably configured to protrude sufficiently from a delivery shaft distal portion 30 as to press into a vaginal fornix 96 or other tissue effective to approach and to begin to compress a blood vessel. A delivery shaft distal extension 40 may extend up to about 3 inches or more from a delivery shaft distal portion 30, and preferably extends up to about 2 inches from a delivery shaft distal portion 30.

A deployment member length 56 may be between about 3 inches and about 18 inches, and is preferably between about 4 inches and about 15 inches. A deployment member inner diameter 46 is preferably configured to fit around a delivery shaft 16 so as to enable at least longitudinal movement of a deployment member 18 which at least partially encloses a delivery shaft 16. Thus, a deployment member inner diameter 46 may be between about 0.9 inch and about 4.1 inches, and is preferably between about 1.3 inches and about 3.1 inches, effective to slip around a delivery shaft.

Constrictor widths 66 and lengths 68 are preferably sized to accommodate a cervix 94 of a female patient, which is typically between about 0.75 inch and about 2 inch in diameter. Thus, for example, in an expanded first configuration a constrictor width 66 may be between about 0.5 inch and about 4 inches, preferably between about 0.7 inch and about 3 inches, more preferably between about 0.75 inch and about 2 inches. A constrictor length 68 may be between about 0.5 inch and about 3 inches, preferably between about 0.5 inch and about 2 inches, more preferably between about 0.75 inch and about 1.5 inches. A loop end 62 of a pressure-applying member 60 is preferably a rounded loop end 62, and may have a radius of between about 0.2 inch and about 1 inch, preferably between about 0.25 inch and about 0.75 inch. Constrictor widths 66 and lengths 68 may also be sized to accommodate target tissues or tissue structures other than a cervix 94 and a uterus 90.

A delivery shaft outer diameter 36 may be between about 0.5 inch and about 4 inches, preferably between about 0.7 inch and about 3 inches, more preferably between about 0.75 inch and about 2 inches. In addition, a constrictor 14 is preferably configured to be carried on an outer surface of a delivery shaft 16 and to be pushed off the delivery shaft 16 by a deployment member 18; widths 66 and lengths 68 are thus preferably sized to accommodate being carried on and delivered from an outer surface of a delivery shaft 16.

A constrictor 14 is preferably sized to be carried on an outer surface of a delivery shaft 16 when in an expanded first configuration; after delivery from a delivery shaft 16 onto a cervix 94 and/or uterus 90, a constrictor 14 preferably assumes a second, contracted configuration effective to apply pressure to a cervix 94 and uterus 90. A constrictor width 66 may decrease by between about 0.1 inch and about 1.5 inch, preferably by between about 0.25 inches and about 1 inch, in going from an expanded first configuration to a contracted second configuration.

Devices according to the present invention permit simultaneous identification and occlusion of a uterine artery in a non-invasive manner, and lower the level of skill needed to identify and occlude the artery because the devices and methods do not require surgical intervention to perform the occlusion.

The present invention also relates to devices, systems, and processes which can be useful in treating dysfunctional uterine bleeding (DUB). Other aspects of the present invention relate to treating a patient who is diagnosed with DUB by compressing one or both uterine arteries, either serially or simultaneously, so that the uterine blood supply is greatly diminished or completely cut off. Without the blood supplied by the uterine arteries, the uterus stops bleeding, which can permit the medical practitioner to better diagnose the patient's condition. The reduction in blood flow resulting form uterine artery occlusion may be itself a treatment for DUB; that is, the DUB will not reoccur upon reestablishment of the blood supply to the uterus through the uterine arteries, the uterus being 'reset' by going through a period of induced anoxia or hypoxia.

The present invention also includes as an aspect the treatment of bleeding associated with Caesarian section. Devices and/or methods of the present invention can be used to slow or stop blood flow to the uterus through the uterine arteries immediately after a baby is delivered by Caesarian section. Subsequently, Caesarian incision repair can be performed in a manner that optimizes surgical closure without worry about blood loss control at the time of closure.

The present invention also includes as an aspect the treatment of bleeding associated with Post Partum Hemorrhage (PPH). PPH is defined in the medical literature as the estimated loss of more than 500 ml of blood following delivery of a baby. According to aspects of the present invention, when it is recognized that bleeding has not stopped normally as it should after delivery, devices and/or methods in accordance with the present invention can be employed as described herein to slow or stop PPH. Immediately postpartum, a female patient's cervix and related anatomy are typically larger and in a different state as compared to the size and physical characteristics typically found at other times. In some embodiments a single constrictor 14 may be applied in order to occlude both uterine arteries for the treatment of PPH; such constrictors 14 would preferably be larger than constrictors 14 employed for other treatments (e.g., uterine fibroids). In alternative embodiments, two constrictors 14 may be applied for the treatment of PPH, one for each uterine artery; such constrictors 14 would preferably be smaller than constrictors 14 employed for other treatments such as uterine fibroids.

While particular forms of the invention have been illustrated and described, it will be apparent that various modifications can be made without departing from the spirit and scope of the invention. Accordingly, it is not intended that the invention be limited to the specific embodiments illustrated. It is therefore intended that this invention to be defined by the scope of the appended claims as broadly as the prior art will permit, and in view of the specification if need be. Moreover, those skilled in the art will recognize that features shown in one embodiment may be utilized in other embodiments. Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety.

What is claimed is:

1. A uterine artery occlusion device, comprising:
   a deployable constrictor having an interior configured to receive a female patient's uterine cervix and having at least one pressure-applying portion having a pressure-applying surface configured to apply pressure to the patient's uterine cervix or a vaginal surface to thereby occlude at least one of the patient's uterine arteries;
   an elongated delivery shaft configured to intravaginally advance said constrictor to the patient's uterine cervix;
   a deployment member configured to deploy said constrictor from said delivery shaft about the patient's uterine cervix so that pressure applied by constriction of the pressure applying surface of the constrictor occludes at least one of the patient's uterine arteries; and
   at least one locating sensor provided on a distal portion of the device configured to detect a blood vessel.

2. The uterine artery occlusion device of claim 1, wherein said deployable constrictor has an expanded configuration configured to receive a patient's uterine cervix, and a contracted configuration configured to apply pressure to the cervix or a vaginal surface after deployment of said deployable constrictor from said delivery shaft to occlude at least one of the patient's uterine arteries.

3. The uterine artery occlusion device of claim 1, wherein said deployable constrictor comprises a wirefom.

4. The uterine artery occlusion device of claim 3, wherein said wireform comprises a resilient wireform.

5. The uterine artery occlusion device of claim 1, wherein said locating sensor comprises a Doppler ultrasound sensor.

6. The uterine artery occlusion device of claim 5, wherein said Doppler sensor is configured to sense ultrasound energy having a frequency of between about 5 MHz and about 20 MHz.

7. The uterine artery occlusion device of claim 5, wherein said Doppler ultrasound sensor is configured to sense ultrasound energy having a frequency of between about 6 MHz and about 10 MHz.

8. The uterine artery occlusion device of claim 1, wherein at least one locating sensor is disposed on said delivery shaft.

9. The uterine artery occlusion device of claim 1, wherein at least one locating sensor is disposed on a pressure-applying portion of said constrictor.

10. The uterine artery occlusion device of claim 1, wherein said constrictor has at least two opposing pressure-applying portions configured to apply pressure to the patient's uterine cervix or vaginal surface to occlude both of the patient's uterine arteries when deployed around the patient's cervix.

11. The uterine artery occlusion device of claim 1, wherein said deployable constrictor comprises a wireform having at least one loop configured to apply pressure to the patient's cervix or a vaginal surface.

12. The uterine artery occlusion device of claim 1, wherein said deployable constrictor comprises a wireform having a double loop configuration configured to apply pressure to the patient's cervix or a vaginal surface.

13. The uterine artery occlusion device of claim 12, wherein loops of said wireform have loop lengths oriented substantially along a longitudinal direction.

14. The uterine artery occlusion device of claim 11, wherein said wireform is formed of a resilient material.

15. The uterine artery occlusion device of claim 14, wherein said at least one loop configured to apply pressure to a cervix or a uterus has a loop length of between about 0.5 inch and about 2 inch.

16. The uterine artery occlusion device of claim 15, wherein said loop length comprises a length of between about 0.75 inch and about 1.5 inch.

17. The uterine artery occlusion device of claim 1, wherein said sensor has a sensing direction that is substantially parallel to said longitudinal direction.

18. The uterine artery occlusion device of claim 1, wherein said delivery shaft comprises a lumen configured to allow passage of a guide therethrough.

19. The uterine artery occlusion device of claim 18, wherein said guide comprises a tenaculum.

20. The uterine artery occlusion device of claim 1, wherein said constrictor is configured to apply a pressure of between about 3 pound per square inch (psi) and about 200 psi to said cervix or vaginal surface.

21. The uterine artery occlusion device of claim 20, wherein said constrictor is configured to apply a pressure of between about 5 psi and about 80 psi to said cervix or vaginal surface.

22. The uterine artery occlusion device of claim 21, wherein said constrictor is configured to apply a pressure of between about 7 psi and about 10 psi to said cervix or vaginal surface.

23. A system for occluding a blood vessel for use by an operator, comprising:
   a blood vessel occlusion device, comprising:
      a deployable constrictor having at least one pair of opposed pressure-applying members having a first configuration to receive a female patient's cervix and a second configuration to apply pressure to the patient's cervix or uterus to occlude at least one of the patient's uterine arteries;
      a delivery shaft configured to intravaginally advance said deployable constrictor in a first configuration to receive at least in the patient's cervix, said delivery shaft having a longitudinal axis defining a longitudinal direction;
      a deployment member configured to deploy the deployable constrictor from the delivery shaft effective that said deployable constrictor assumes a second configuration about at least part of the patient's cervix and to thereby at least partially occlude a uterine artery;
      a sensor configured to detect a blood vessel and disposed on at least one of said delivery shaft and said deployable constrictor; and
      a sensor controller operatively connected to said sensor and comprising a source of power.

24. The system of claim 23, wherein said constrictor comprises at least two pressure-applying members.

25. The system of claim 23, wherein said sensor comprises a Doppler ultrasound sensor.

26. The system of claim 23, wherein said sensor controller is configured to provide an audible signal.

27. The system of claim 23, wherein said constrictor comprises at least one loop configured to apply pressure to a cervix or uterus.

28. A system for occluding a a female patient's uterine artery, comprising:
   an occlusion device, comprising:
      a deployable constrictor having at least one pair of opposed pressure-applying members which have a first configuration to receive a female patient's cervix and a second configuration to apply pressure to the patient's cervix or vaginal surface to occlude at least one of the patient's uterine arteries;
      a delivery shaft configured to intravaginally advance said deployable constrictor in the first configuration to receive at least in the patient's cervix, said delivery shaft having a longitudinal axis defining a longitudinal direction;
      a deployment member configured to deploy the deployable constrictor from the delivery shaft after receiving the female patient's cervix and assuming the second configuration to apply pressure about at least part of the patient's cervix and to thereby at least partially occlude at least one of the uterine arteries;
      a sensor configured to detect at least one uterine artery and disposed on at least one of said delivery shaft and said deployable constrictor; and
      a guide configured to engage a cervix.

29. The system of claim 28, wherein said constrictor comprises at least two pressure-applying members.

30. The system of claim 28, wherein said guide comprises a tenaculum.

31. The system of claim 28, wherein said sensor comprises a Doppler ultrasound sensor.

32. The system of claim 28, wherein said constrictor comprises a wireform configured to apply pressure to the female patient's cervix or vaginal surface.

33. The system of claim 29, wherein the wireform has at least two pressure-applying members comprising loops of resilient material configured to compress the female patient's cervix or vaginal surface.

34. A method of occluding at least one uterine artery of a female patient, comprising:
   providing a uterine artery occlusion device having an elongated delivery shaft, a deployable constrictor mounted on the delivery shaft which has at least one pair of opposed pressure-applying members with a first mounted configuration to receive a female patient's cervix and a second deployed configuration to apply pressure to the patient's cervix or vaginal tissue to occlude at least one of the patient's uterine arteries and having a blood flow sensor to detect at least one uterine artery;
   locating the deployable constrictor in the first mounted configuration about the female patient's cervix;
   detecting a uterine artery with the blood flow sensor; and
   deploying said deployable constrictor about said cervix in said second configuration to apply pressure to said cervix or vaginal surface and to occlude a uterine artery.

35. The method of claim 34, further comprising detecting a change in blood flow through said uterine artery with said sensor.

36. The method of claim 34, further comprising engaging said cervix with a guide.

37. The method of claim 36, wherein said guide comprises a tenaculum.

38. The method of claim 34, wherein said sensor comprises a Doppler ultrasound blood flow sensor.

39. The method of claim 34, wherein said deployable constrictor occludes said uterine artery for only a limited time.

40. The method of claim 39, wherein said limited time comprises a time of between about 0.5 hours and about 24 hours.

41. The method of claim 40, wherein said limited time comprises a time of between about 1 hour and about 9 hours.

42. The method of claim 35, wherein said pressure comprises a pressure of between about 3 psi and about 200 psi.

43. A uterine artery occlusion device, comprising:
   a deployable constrictor means configured to receive and apply pressure to a patient's cervix or vaginal surface and thereby occlude at least one of the patient's uterine arteries;
   a delivery means configured to intravaginally advance said constrictor means to the patient's cervix;
   a deployment means configured to deploy said constrictor means from said delivery means and to place said constrictor means about the cervix or uterus effective to occlude at least one of the patient's uterine arteries; and
   at least one locating sensor means configured to detect a blood vessel.

* * * * *

Dedication

7,172,603 B2 — Fred Burbank, Laguna Niguel, CA (US); Michael L. Jones, San Clemente, CA (US); Greig E. Altieri, Laguna Beach, CA (US); Ed Olson, Lake Forest, CA (US). DEPLOYABLE CONSTRICTOR FOR UTERINE ARTERY OCCLUSION. Patent dated February 6, 2007. Dedication filed November 2, 2011, by the assignee, Vascular Control Systems, Inc. any patent Hereby dedicates to the Public, the remaining term, including term extension, of said patent.

*(Official Gazette, August 14, 2012)*